United States Patent
Kessler et al.

(10) Patent No.: US 9,839,073 B2
(45) Date of Patent: Dec. 5, 2017

(54) MULTIFUNCTIONAL CNT-ENGINEERED STRUCTURES

(71) Applicants: Metis Design Corporation, Boston, MA (US); Massachusetts Institute of Technology, Cambridge, MA (US)

(72) Inventors: Seth S. Kessler, Newton, MA (US); Ajay Raghavan, Mountain View, CA (US); Brian L. Wardle, Lexington, MA (US)

(73) Assignees: Metis Design Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/250,340

(22) Filed: Aug. 29, 2016

(65) Prior Publication Data

US 2017/0019954 A1   Jan. 19, 2017

Related U.S. Application Data

(63) Continuation of application No. 15/067,062, filed on Mar. 10, 2016, which is a continuation of application
(Continued)

(51) Int. Cl.
*H05B 1/02* (2006.01)
*H05B 3/14* (2006.01)
(Continued)

(52) U.S. Cl.
CPC ............ *H05B 3/145* (2013.01); *B64D 15/12* (2013.01); *B64D 15/20* (2013.01); *G01N 25/00* (2013.01);
(Continued)

(58) Field of Classification Search
CPC .. B82Y 99/00; G01N 25/00; H05B 2203/003; H05B 3/145; Y10S 977/742–977/752;
(Continued)

(56) References Cited

U.S. PATENT DOCUMENTS 2,884,786 A   5/1959   Burk
3,594,775 A   7/1971   Fox
(Continued)

FOREIGN PATENT DOCUMENTS

WO   2004/065926 A1   8/2004
WO   2006/004733 A1   1/2006
(Continued)

OTHER PUBLICATIONS

Qiu, J., et al., "Carbon nanotube integrated multifunctional multiscale composites," Nanotechnology, 2007. 18(27): p. 275708.
(Continued)

*Primary Examiner* — Sang Y Paik
(74) *Attorney, Agent, or Firm* — McCarter & English, LLP; David R. Burns

(57) ABSTRACT

Various applications for structured CNT-engineered materials are disclosed herein. In one application, systems are disclosed, wherein a structured CNT-engineered material forms at least part of an object capable of providing its own structural feedback. In another application, systems are disclosed, wherein a structured CNT-engineered material forms at least part of an object capable of generating heat. In yet another application, systems are disclosed, wherein a structured CNT-engineered material forms at least part of an object capable of functioning as an antenna, for example, for receiving, transmitting, absorbing and/or dissipating a signal. In still another application, systems are disclosed,
(Continued)

wherein a structured CNT-engineered material forms at least part of an object capable of serving as a conduit for thermal or electrical energy.

30 Claims, 12 Drawing Sheets

Related U.S. Application Data

No. 14/808,949, filed on Jul. 24, 2015, now abandoned, which is a continuation of application No. 13/014,603, filed on Jan. 26, 2011, now Pat. No. 9,091,657.

(60) Provisional application No. 61/298,385, filed on Jan. 26, 2010.

(51) Int. Cl.
| | |
|---|---|
| *H01B 1/02* | (2006.01) |
| *G01N 25/72* | (2006.01) |
| *G01N 25/00* | (2006.01) |
| *B64D 15/20* | (2006.01) |
| *B64D 15/12* | (2006.01) |
| *C08K 3/04* | (2006.01) |
| *B82Y 99/00* | (2011.01) |
| *B64C 1/00* | (2006.01) |
| *B64D 45/00* | (2006.01) |

(52) U.S. Cl.
CPC ............ *G01N 25/72* (2013.01); *H01B 1/02* (2013.01); *B64C 2001/0072* (2013.01); *B64D 2045/0085* (2013.01); *B82Y 99/00* (2013.01); *C08K 3/04* (2013.01); *C08K 3/041* (2017.05); *H05B 2203/003* (2013.01); *H05B 2203/021* (2013.01); *H05B 2214/02* (2013.01); *H05B 2214/04* (2013.01); *Y10S 977/742* (2013.01)

(58) Field of Classification Search
CPC ... C08K 3/04; C08K 9/08; C09D 5/24; C09D 7/1291
USPC ............... 219/200, 542–549, 490, 509, 510; 977/742; 73/645–648
See application file for complete search history.

(56) References Cited

U.S. PATENT DOCUMENTS

| | | | |
|---|---|---|---|
| 4,170,677 A | 10/1979 | Hutcheson | |
| 6,180,925 B1 | 1/2001 | Moore et al. | |
| 6,236,025 B1 | 5/2001 | Berkcan et al. | |
| 6,276,214 B1 | 8/2001 | Kimura et al. | |
| 6,514,453 B2 | 2/2003 | Vigliotti et al. | |
| 6,882,051 B2 | 4/2005 | Majumdar et al. | |
| 6,924,335 B2* | 8/2005 | Fan ........................ | B82Y 30/00 |
| | | | 165/185 |
| 6,986,853 B2 | 1/2006 | Glatkowski et al. | |
| 7,057,881 B2 | 6/2006 | Chow et al. | |
| 7,106,310 B2 | 9/2006 | Knowles et al. | |
| 7,217,374 B2 | 5/2007 | Watanabe et al. | |
| 7,439,877 B1 | 10/2008 | Jarvinen | |
| 7,537,825 B1 | 5/2009 | Wardle et al. | |
| 7,659,493 B2 | 2/2010 | Reusche et al. | |
| 7,673,521 B2 | 3/2010 | Ajayan et al. | |
| 7,786,736 B2 | 8/2010 | Thostenson et al. | |
| 7,968,824 B2 | 6/2011 | Lee et al. | |
| 8,146,861 B2 | 4/2012 | Lengsfeld et al. | |
| 8,257,678 B2 | 9/2012 | Steiner, III et al. | |
| 8,525,507 B2 | 9/2013 | Aldraihem | |
| 8,684,595 B2 | 4/2014 | Wardle et al. | |
| 8,931,740 B2 | 1/2015 | Nordin et al. | |
| 9,091,657 B2* | 7/2015 | Kessler ................... | G01N 25/72 |
| 2003/0205671 A1 | 11/2003 | Thomas et al. | |
| 2004/0206748 A1* | 10/2004 | Dreher .................... | B26B 13/24 |
| | | | 219/494 |
| 2005/0036905 A1 | 2/2005 | Gokturk | |
| 2005/0116336 A1 | 6/2005 | Chopra et al. | |
| 2005/0284232 A1 | 12/2005 | Rice | |
| 2006/0169788 A1 | 8/2006 | Empedocles et al. | |
| 2007/0041887 A1 | 2/2007 | Veedu et al. | |
| 2007/0132043 A1 | 6/2007 | Bradley et al. | |
| 2007/0138010 A1 | 6/2007 | Ajayan | |
| 2007/0170170 A1 | 7/2007 | Sata et al. | |
| 2007/0222472 A1 | 9/2007 | Raravikar et al. | |
| 2008/0039557 A1 | 2/2008 | Li et al. | |
| 2008/0075954 A1 | 3/2008 | Wardle et al. | |
| 2008/0170982 A1 | 7/2008 | Zhang et al. | |
| 2008/0290080 A1 | 11/2008 | Weiss | |
| 2009/0121727 A1 | 5/2009 | Lynch et al. | |
| 2009/0140098 A1* | 6/2009 | Lengsfeld ............... | B64D 45/02 |
| | | | 244/121 |
| 2009/0199569 A1* | 8/2009 | Petrenko ................. | B64D 15/12 |
| | | | 62/3.1 |
| 2009/0272935 A1 | 11/2009 | Hata et al. | |
| 2009/0277897 A1 | 11/2009 | Lashmore et al. | |
| 2009/0311166 A1 | 12/2009 | Hart et al. | |
| 2010/0196695 A1 | 8/2010 | Garcia et al. | |
| 2010/0249877 A1 | 9/2010 | Naughton | |
| 2010/0255303 A1 | 10/2010 | Wardle et al. | |
| 2010/0270704 A1* | 10/2010 | Feng ....................... | B82Y 30/00 |
| | | | 264/291 |
| 2012/0292439 A1 | 11/2012 | Hallander et al. | |
| 2013/0058859 A1 | 3/2013 | Steiner, III et al. | |
| 2014/0269830 A1 | 9/2014 | Wardle et al. | |

FOREIGN PATENT DOCUMENTS

| | | |
|---|---|---|
| WO | 2007/136264 A1 | 11/2007 |
| WO | 2007/136755 A2 | 11/2007 |
| WO | 2008/054541 A2 | 5/2008 |
| WO | 2008/135606 A1 | 11/2008 |
| WO | 2009/029218 A2 | 3/2009 |
| WO | 2009/141472 A1 | 11/2009 |

OTHER PUBLICATIONS

Raghavan, A., et al., "Structural Health Monitoring using Carbon Nanotube (CNT) Enhanced Composites," 7th International Workshop on SHM (IWSHM07), Stanford University, Sep. 9-11, 2009.
Roach, D., "Assessing conventional and advanced NDI for composite aircraft," High-Performance Composites 16 (4), 72 (2008).
Sakagami, T., et al., "New Flaw Inspection Technique Based on Infrared Thermal Images under Joule Effect Heating," JSME International Journal, Series A: Mechanics and Material Engineering 37 (4), pp. 380-388 (1994).
Sakagami, T., et al., "Applications of pulse heating thermography and lock-in thermography to quantitative nondestructive evaluations," Infrared Physics & Technology 43, vols. 3-5, pp. 211-218 (2002).
Salvetat, J.-P., et al., "Elastic and Shear Moduli of Single-Walled Carbon Nanotube Ropes," Physical Review Letters, 82(5): pp. 944-947 (1999).
Schulte, K. and A.H. Windle, "Editorial," Composites Science and Technology Carbon Nanotube (CNT)—Polymer Composites, 2007. 67(5): p. 777.
Staszewski, W. J., et al., "Fatigue crack detection in metallic structures with Lamb waves and 3D laser vibrometry," Measurement Science & Technology, 2007. 18(3): p. 727-739.
Thostenson, E.T., et al., "Nanocomposites in Context," Composites Science and Technology, vol. 65(3-4):491-516, 2005.
Thostenson, E.T., et al., "Real-time in situ sensing of damage evolution in advanced fiber composites using carbon nanotube networks" Nanotechnology, 2008, 19(21): p. 215713.
Thostenson, E.T., T.-W.Chou, "Carbon Nanotube Networks: Sensing of Distributed Strain and Damage for Life Prediction and Self-Healing." Advanced Materials, 2006. 18(21): p. 2837-2841.

(56) References Cited

OTHER PUBLICATIONS

Thostenson, E.T., Z. Ren, and T.-W. Chou, "Advances in the science and technology of carbon nanotubes and their composites." Composites Science & Technology, 2001. 61(13): p. 1899-1912.

Treacy, M. M. J., et al, "Exceptionally high Young's modulus observed for individual carbon nanotubes." Nature, 1996. 381(6584): p. 678-680.

Triantafillou, T. C., "Strengthening of Structures with Advanced FRPs," Progress in Structural Engineering and Materials, 1, pp. 126-134 (1998).

Vaia, R. et al., "Adaptive Composites," Science 319, 420-421 (2008).

Veedu, V.P., et al., "Multifunctional composites using reinforced laminae with carbon-nanotube forests." Nature Materials, 2006. 5(6): p. 457-462.

Wardle B, et al., "Fabrication and Characterization of Ultrahigh-Volume-Fraction Aligned Carbon Nanotube-Polymer Composites" Advanced Materials, vol. 20, pp. 2707-2714 (2008).

Wardle, B.L., et al., "Particle and Fiber Exposures During Processing of Hybrid Carbon-Nanotube Advanced Composites." in 2008 SAMPE Fall Technical Conference. Sep. 2008. Memphis, TN.

Wei, B.Q., et al., "Reliability and current carrying capacity of carbon nanotubes." Applied Physics Letters, 2001. 79(8): p. 1172-1174.

Weritz, F., et al., "Investigation of Concrete Structures with Pulse Phase Thermography," Materials and Structures, 38 (2005), pp. 843-849.

Wicks, S.S., et al. "Fracture Toughness of a Woven Advanced Composite Reinforced with Aligned Carbon Nanotubes." in 50th AIAA/ASME/ASCE/AHS/ASC Structures, Structural Dynamics, and Materials Conference. 2009. Palm Springs, CA.

Wicks, S.S., et al., "Interlaminar and Intralaminar Reinforcement of Composite Laminates with Aligned Carbon Nanotubes.," Composite Science and Technology, vol. 70, pp. 20-28 (2010).

Written Opinion dated Oct. 13, 2009 in PCT/ES2009/000280.

Written Opinion issued in International Application No. PCT/US2011/022625, dated Jul. 28, 2011.

Yamamoto, N. et al., "High-yield growth and morphology control of aligned carbon nanotubes on ceramic fibers for multifunctional enhancement of structural composites." Carbon 47 (3), 551 (2009).

Yamamoto, N., et al., "Mechanical, Thermal, and Electrical Properties of Woven Laminated Advanced Composites Containing Aligned Carbon Nanotubes," 17th International Conference on Composite Materials (ICCM), Edinburgh, Scotland, Jul. 27-31, 2009.

Yi, Y. B., et al., "Statistical geometry of random fibrous networks, revisited: Waviness, dimensionality, and percolation," Journal of Applied Physics, 96(3), pp. 1318-1327 (2004).

Yu, M.-F., et al., "Strength and Breaking Mechanism of Multiwalled Carbon Nanotubes Under Tensile Load," Science, 287(5453), pp. 637-640 (2000).

Zahn M, "Optical, Electrical and Electromechanical Measurement Methodologies of Fields, Charge and Polarization in Dielectrics," IEEE Transactions on Dielectrics and Electrical Insulation, vol. 5, No. 5, pp. 627-650, Oct. 1998.

Zhang, W., et al. "Carbon nanotube/polycarbonate composites as multifunctional strain sensors." Journal of Nanoscience and Nanotechnology, 2006. 6: p. 960-964.

Zhu, J., et al., "Processing a glass fiber reinforced vinyl ester composite with nanotube enhancement of interlaminar shear strength." Composites Science and Technology, 2007. 67(7-8): p. 1509-1517.

Ahmed, T. J., et. al., "Heat emitting layers as an aid for for enhancing NDE of aircraft composite structures," 49th AIAA/ASME/ASCE/AHS/ASC Structures, Structural Dynamics and Materials Conference. Apr. 7, 2008, vol. 4, pp. 1 and 2081-2089.

Ahmed, T. J., et. al., "Heat emitting layers for enhancing NDE of composite structures," Composites Part A, vol. 39, Issue 6, pp. 1025-1036, Jun. 2008.

Ajayan, P.M. and J.M. Tour, "Nanotube composites," Nature. vol. 447, pp. 1066-1068, Jun. 2007.

Bar-Cohen, Y. "NDE of fiber-reinforced composite materials—A Review," Mater. Eval., vol. 44, pp. 446-454 (1986).

Bar-Cohen, Y., "Emerging NDE Technologies and Challenges at the Beginning of the 3rd Millennium." Mater. Eval., vol. 5, (2000), pp. 17-30.

Barber, D., et al., "Health Monitoring of Aligned Carbon Nanotube (CNT) Enhanced Composites," Proceedings of the SAMPE Fall Technical Conference, Wichita, KS, Oct. 19-22, 2009.

Barreiro, A, et al., "Subnanometer Motion of Cargoes Driven by Thermal Gradients Along Carbon Nanotubes." Science, 320, 775-777 (2008).

Baughman, R. H., et. al., "Carbon Nanotubes—the Route Toward Applications," Science, vol. 297, (2002), pp. 787-792.

Beyakrova, E., et al., "Multiscale carbon nanotube-carbon fiber reinforcement for advanced epoxy composites," Langmuir, 2007. 23(7): p. 3970-3974.

Boger L, et al., "Load and Health Monitoring in Glass Fibre Reinforced Composites with an Electrically Conductive Nanocomposite Epoxy Matrix," Composites Science and Technology, 68 1886-1894 (2008).

Bouvier, C., "Investigating Variables in Thermographic Composite Inspection." Mater. Eval. 53 544-551 (1995).

Cebeci, H, et al., "Multifunctional Properties of High Volume Fraction Aligned Carbon Nanotube Polymer Composites with Controlled Morphology," Composites Science and Technology 69 2649-2656 (2009).

Coleman, J. N., et. al., "Small but strong: A review of the mechanical properties of carbon nanotube-polymer composites," Carbon 44 (9), 1624 (2006).

Dharap, P., et al., "Nanotube film based on single-wall carbon nanotube for strain sensing," Nanotechnology, 15, p. 379-382 (2004).

Du, F. M., "Effect of Nanotube Alignment on Percolation Conductivity in Carbon Nanotube/Polymer Composites," Physical Review B, vol. 72(12), 121404(R) (2005).

Dzenis, Y., "Structural Nanocomposites," Science, 319, pp. 419-420 (2008).

Fernandez, J.E., "Materials for Aesthetic, Energy-Efficient, and Self-Diagnostic Buildings," Science, 315, pp. 1807-1810 (2007).

Fiedler, B., et al., "Can Carbon Nanotubes be used to Sense Damage in Composites?" Annales de Chimie Science des Matériaux 22 81-94 (2004).

Garcia, E.J., et al., "Fabrication & Multifunctional Properties of a Hybrid Laminate with Aligned Carbon Nanotubes Grown in Situ" Composites Science & Technology, 2008.68(9): p. 2034-2041.

Garcia, E.J., et al., "Fabrication and Multifunctional Properties of High Volume Fraction Aligned Carbon Nanotube Thermoset Composites," Journal of Nano System &Technology 1 1-11 (2009).

Garcia, E.J., et al., "Fabrication and Testing of Long Carbon Nanotubes Grown on the Surface of Fibers for Hybrid Composites." in 47th AIAA/ASME/ASCE/AJS/ASC Structures, Structural Dynamics, and Materials Conference. 2006. Newport, R.I.

Garcia, E.J., et al., "Fabrication of composite microstructures by capillarity-driven wetting of aligned carbon nanotubes with polymers." Nanotechnology, 2007. 18(16): p. 165602.

Garcia, E.J., et al., "Long Carbon Nanotubes Grown on the Surface of Fibers for Hybrid Composites," AIAA Journal, vol. 46, No. 6, 2008, pp. 1405-1412.

Giorleo, G. et al, "Comparison Between Pulsed and Modulated Thermography in Glass-Epoxy Laminates.," NDT & E International, vol. 35, pp. 287-292 (2002).

Giorleo, G., et al., "Location and Geometry of Defects in Composite Laminates from Infrared Images," Journal of Materials and Performance, vol. 7, pp. 367-374 (1998).

Gojny, F.H., et al., "Carbon nanotube-reinforced epoxy-composites: enhanced stiffness & fracture toughness at low nanotube content." Composites Science & Technology, 2004. 64(15): p. 2363-2371.

Goldfine, N., et al, "Conformable Eddy-Current Sensors and Arrays for Fleetwide Gas Turbine Component Quality Assessment," ASME Turbo Expo Land, Sea, & Air, Jun. 4-7, 2001, New Orleans, Louisiana.

(56) References Cited

OTHER PUBLICATIONS

Goldfine, N., et al, "Conformable Eddy-Current Sensors and Arrays for Fleetwide Gas Turbine Component Quality Assessment," Journal of Engineering for Gas Turbines and Power, vol. 124, (2002), pp. 904-909.
Goldfine, N., et al., "Conformable Eddy Current Sensors and Methods for Gas Turbine Inspection and Health Monitoring," Gas Turbine Materials Technology 105-114 (1999).
Guzman De Villoria, R. et al., "Mechanical model to evaluate the effect of the dispersion in nanocomposites," Acta Mater. 55 (9), 3025 (2007).
Guzman De Villoria, R., et al., "High-Yield Growth of Vertically Aligned Carbon Nanotubes on a Continuously Moving Substrate," 2009 Nanotechnology 20 405611 (8pp).
Hogg, P.J., "Composites in Armor," Science, 314, pp. 1100-1101 (2006).
Hou, T.-C., Loh, K. J., and Lynch, J. P., "Spatial Conductivity Mapping of Carbon Nanotube Composite Thin Films by Electrical Impedance Tomography for Sensing Applications," Nanotechnology 18, 315501 (9pp) (2007).
Hung Y. Y., et al., "Review and Comparison of Shearography and Active Thermography for Nondestructive Evaluation," Materials Science and Engineering: R, 64, pp. 73-112 (2009).
International Preliminary Report on Patentability dated Jul. 31, 2012 for PCT/US2011/022625 (M0925.7040WO00).
International Search Report dated Oct. 13, 2009 in PCT/ES2009/000280.
International Search Report issued in International Application No. PCT/US2011/022625, dated Jul. 28, 2011.
Invitation to Pay Additional Fees dated May 13, 2011 for PCT/US2011/022625 (M0925.7040WO00).
Jeong, Y. J. et al., "Synergistic Strengthening Effect of Ultrafine-Grained Metals Reinforced with Carbon Nanotubes," Small, vol. 3, Issue 5, pp. 840-844 (2007).
Kessler S., et al., "Damage detection in composite materials using Lamb wave methods," Smart Materials and Structures, vol. 11, pp. 269-278 (2002).
Koerner, H., et al., "Remotely Actuated Polymer Nanocomposites-Stress-Recovery of Carbon-Nanotube-Filled Thermoplastic Elastomers," Nature Materials, vol. 3, pp. 115-120 (2004).
Kupke, M., et al., "Non-Destructive Testing of FRP by D.C. and A.C. Electrical Methods," Composites Science and Technology, vol. 61, pp. 837-847 (2001).
Li, C., E.T. Thostenson, and T.-W. Chou, "Sensors and actuators based on carbon nanotubes and their composites: A review." Composites Science and Technology, 2008, 68(6): p. 1227-1249.
Li, Z. Q., et al., "Solution of Transient Temperature Field for Thermographic NDT Under Joule Effect Heating," Journal of Heat Transfer 127 (7), 670 (2005).
Loh, K., et al., "Carbon Nanotube Sensing Skins for Spatial Strain and Impact Damage Identification," Journal of Nondestructive Evaluation, 28 (1), 9 (2009).
Mieres, J.M., et al., "Description of a Traffic Bridge of the Cantabrian SpeedWay Made of Composite Materials," Materiales de Construcción vol. 56, pp. 81-86, (2006).
Miravete, A., et al., "Corrosion Study of Fiberglass Rebars Embedded in Concrete: One Case Study," Corrosion 2007 (NACE International), Mar. 11-15, 2007, Nashville, TN. p. 07534.
Musso, S., et al., "Influence of carbon nanotubes structure on the mechanical behavior of cement composites," Compos. Sci. Technol., 69, pp. 1985-1990 (2009).
Nofar, M. et al. "Failure detection and monitoring in polymer matrix composites subjected to static and dynamic loads using carbon nanotube networks," Composites Science and Technology 69, (2009) pp. 1599-1606.
Pop, E. et al., "Thermal Conductance of an Individual Single-Wall Carbon Nanotube above Room Temperature," Nano Lett. 6 (1), pp. 96-100, (2006).
Extended European Search Report by the European Patent Office for EP Application No. 11737604.6 dated May 26, 2017.
U.S. Appl. No. 13/014,603, filed Jan. 26, 2011, Patented.
U.S. Appl. No. 14/808,949, filed Jul. 24, 2015, Abandoned.
U.S. Appl. No. 15/067,062, filed Mar. 10, 2016, Pending.
U.S. Appl. No. 14/678,066, filed Apr. 3, 2015, Pending.

* cited by examiner

Figure 9
a) -5 °C start
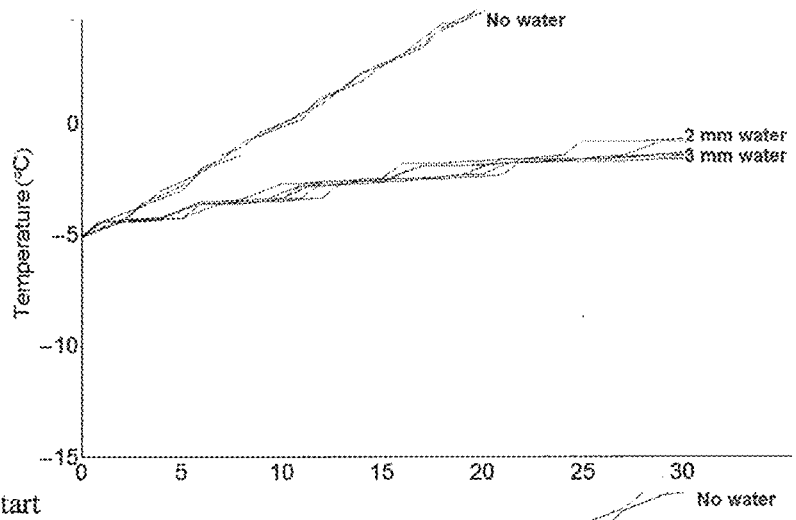
b) -10 °C start
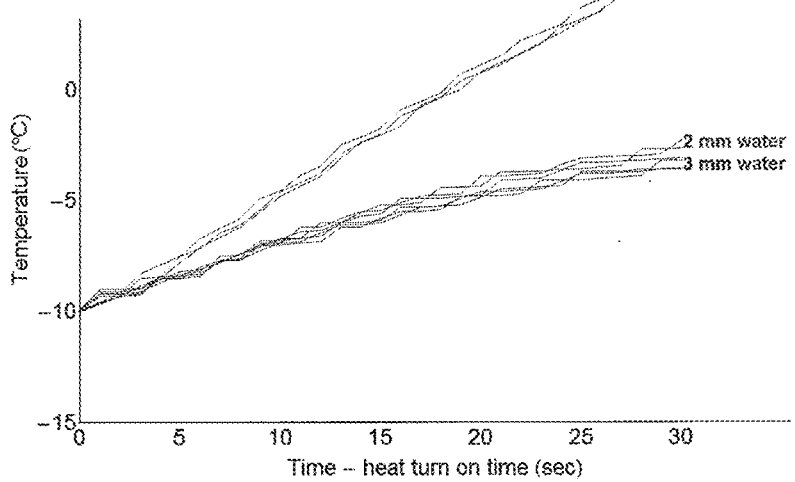
c) -15 °C start
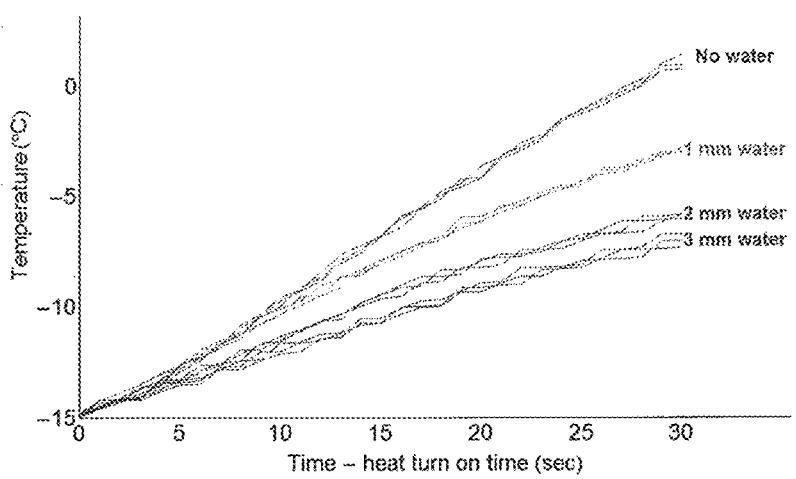

Figure 14
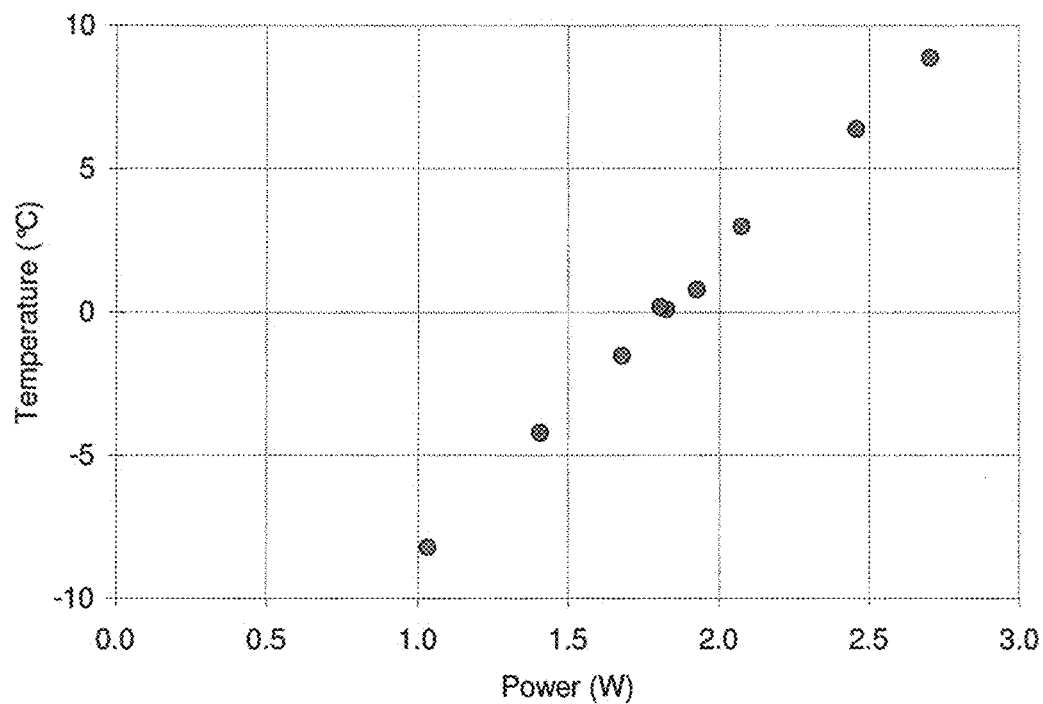
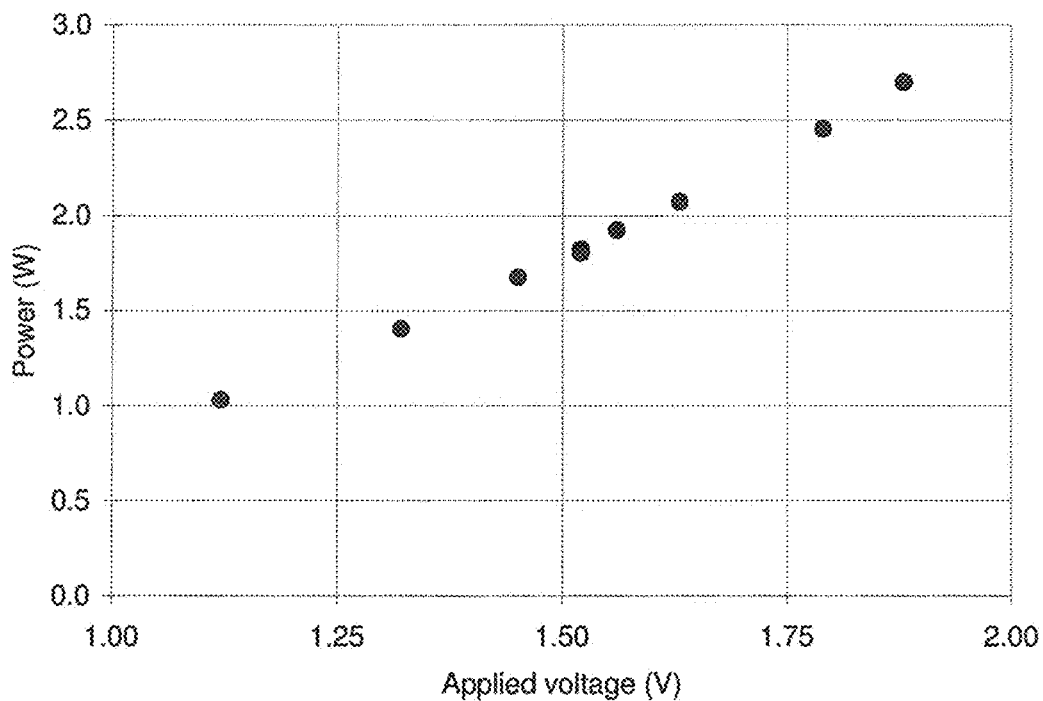

Figure 15
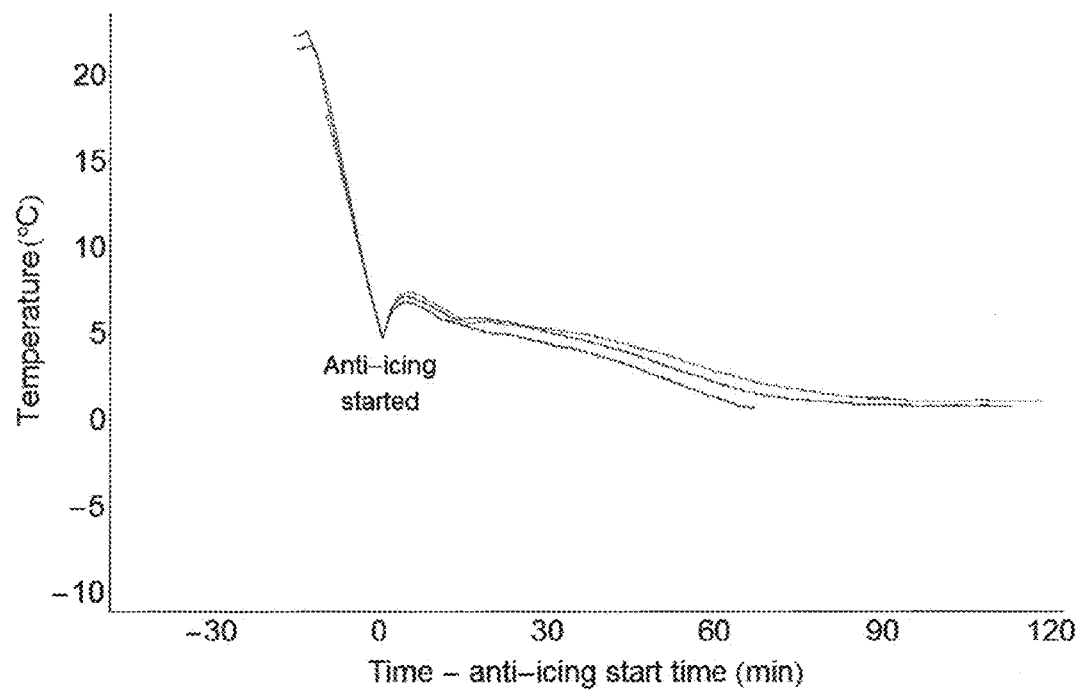
Anti-icing starting from 5 °C following cool-down from room temperature
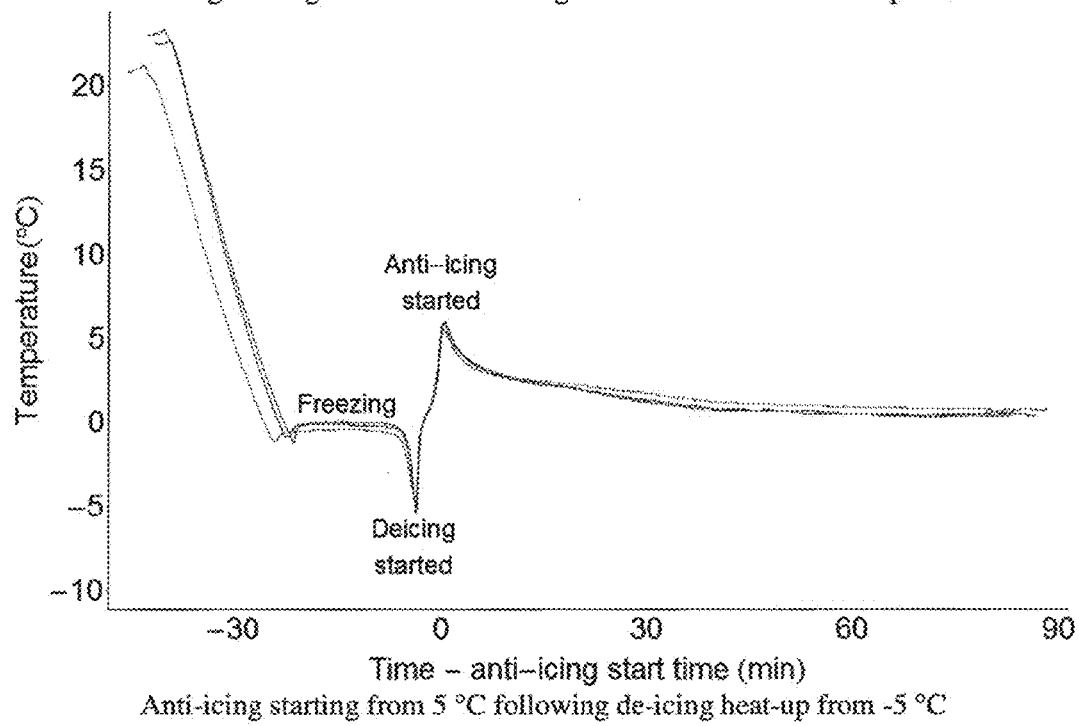
Anti-icing starting from 5 °C following de-icing heat-up from -5 °C

MULTIFUNCTIONAL CNT-ENGINEERED STRUCTURES

CROSS-REFERENCE TO RELATED APPLICATION

This application is a continuation of and claims the benefit of priority to U.S. patent application Ser. No. 15/067,062, filed on Mar. 10, 2016, which is a continuation of and claims the benefit of priority to U.S. patent application Ser. No. 14/808,949, filed on Jul. 24, 2015, which is a continuation of and claims the benefit of priority to U.S. patent application Ser. No. 13/014,603, filed on Jan. 26, 2011, now U.S. Pat. No. 9,091,657, which claims the benefit of priority to U.S. Provisional Patent Application Ser. No. 61/298,385, entitled "Multifunctional CNT-Engineered Structures," filed on Jan. 26, 2010. The entire content of each application is hereby incorporated by reference in its entirety.

STATEMENT OF GOVERNMENT INTEREST

This invention was made with Government support under Contract No. FA9550-09-C-0165 awarded by the Air Force Office of Scientific Research. The Government has certain rights in the invention.

BACKGROUND

Advanced composite materials are increasingly used in applications such as aerospace structure design due to superior stiffness, strength, fatigue resistance, corrosion resistance, etc. In many instances, the use of advanced composite materials may also greatly reduce the number of parts. Composites present challenges for inspection however due to heterogeneity, anisotropy, and the fact that damage is often subsurface. Despite success in the laboratory setting, many non-destructive testing and monitoring techniques, are impractical for real-world inspection of large-area integrated composite structures, for example, due to the size and complexity of the required support equipment. In addition, many components that need frequent monitoring typically reside in limited access areas that would require breaking of factory seals and calibrations to manually inspect. It is clear that new approaches for inspection are necessary.

To facilitate inspection, a structure may advantageously incorporate a distribution of sensors to provide feedback for or on the structure. Such feedback may include event notifications (such as for impact), structural integrity, usage, shape, and/or configuration. Conventional sensors, however, may add weight to a structure and can present electrical connectivity and mechanical coupling challenges. Conventional sensors often present reliability risks (i.e., many sensors fail and/or malfunction in advance of the structure they are monitoring). Thus structures formed from materials which are capable in themselves of providing feedback are highly desirable. Examples of such integrated feedback materials include but are note limited to materials that change resistance values as they are strained, materials that can provide actuation through phase change, ablative materials, and materials that can store energy.

Carbon nanotubes (CNTs) can posses exceptional mechanical stiffness (e.g., ~1 TPa) and strength, as well as excellent electrical conductivity (e.g., ~1000× copper) and piezoresistivity (resistivity change with mechanical strain). Presently, however, it is not possible to produce large specimen (>5 mm) purely of CNTs. Furthermore, due to issues such as agglomeration and poor dispersion, only marginal improvements in mechanical properties are observed for hybrid composites when CNTs are introduced into the bulk matrix. Somewhat better results can be achieved using nanoscale modification of the interface between composite plies, by growing CNTs on the surface of cloth or placing unaligned CNTs at low volume fractions on fibers. However, these approaches do not significantly improve electrical conductivity and thus limit many practical applications.

SUMMARY

New and advantageous applications for structured CNT-engineered materials are disclosed herein. In some embodiments, systems are disclosed, wherein a structured CNT-engineered material forms at least part of an object capable of providing its own structural feedback, for example, structural health feedback. Feedback may also include spatial information, for example, for localizing a point of impact or a damaged area of the object. In other exemplary embodiments, systems are disclosed, wherein a structured CNT-engineered material forms at least part of an object capable of generating heat. The generated heat may be used, for example, for thermographic imaging of the object or other purposes, such as de-icing or maintaining a certain temperature. In yet other exemplary embodiments, systems are disclosed wherein a structured CNT-engineered material forms at least part of an object capable of functioning as an antenna, for example, for receiving, transmitting, absorbing and/or dissipating a signal. In still other embodiments, systems are disclosed, wherein a structured CNT-engineered material forms at least part an object capable of serving as a conduit for thermal or electrical energy.

In exemplary embodiments, systems may include a detection system and/or a control system operationally coupled to a structured CNT network of an object at least part of a structured CNT-engineered material. For example, one or more electrode arrays may be used to couple the structured CNT network to the detection system and/or the control system. In exemplary embodiments, the detection and/or control system may be implemented in whole or in part using computing environment, or processor as described herein. In some embodiments, the detection system may be used to detect electrical conductivity/resistivity across the CNT network, for example, across one or more electrode pairs. In other embodiments, the detection system may be used to detect propagation of an electrical or acoustic signal across the CNT network. In some embodiments, the control system may be used to power the CNT-network, for example, induce a voltage or current across one or more electrode pairs, to generate heat.

In exemplary embodiments a system is disclosed including an object having a portion formed from a structured CNT-engineered material and a control system operationally coupled to the structured CNT network of the CNT-engineered material and configurable or programmable to drive the structured CNT network with electrical energy to maintain or change a temperature of the object. In some embodiments, driving the structured CNT network includes inducing a current through the CNT network. In other embodiments, driving the structured CNT network includes inducing a voltage across the CNT network. In exemplary embodiments, maintaining the temperature of the object includes maintaining the temperature of the object at or above a selected temperature. In exemplary embodiments the object is used to maintain or change a temperature of a substance associated with the object (for example, a substance on, in or otherwise thermally coupled to the object). In some embodiments the temperature of the substance may be maintained at or above a selected temperature so as to prevent a phase transition thereof. In other embodiments, the temperature of the substance may be changed so as to induce a phase transition thereof. In some embodiments, the control system may be configured to change a temperature of the object so as to de-ice the object. In other embodiments, the control system may be configured to change a temperature of the object so as to prevent icing thereof. In some embodiments, the control system may be configured to change a temperature of the object so as to so as to melt a frozen fluid in the system or prevent a fluid in the system from freezing. In some embodiments, the system may include a thermographic imaging system for thermographically imaging the object, for example, to detect a property or characteristic of the object related to structural health of the object. In other embodiments, The system may include a detection system for providing temperature feedback for the object and/or its surroundings. In exemplary embodiments, the control system may be configured to adjust power to the CNT-network based on the temperature feedback. In some embodiments the temperature feedback may include temperature change rate for the object or for a substance associated with the object. In exemplary embodiments the detection system may be configured to determine a property or characteristic, for example, presence/absence, amount, constitution, or the like, of a substance, for example ice, associated with the object based on a temperature change rate of the object or of the substance.

In exemplary embodiments a system is disclosed including an object having a portion formed from a structured CNT-engineered material and a configurable or programmable detection system operationally coupled to the CNT network of the structured CNT-engineered material to detect a change in a physical property or characteristic of the object. Advantageously the physical property or characteristic may include spatial data, relating for example, to one or more of location, size, shape and distribution of the physical property or characteristic. In some embodiments, detecting the change in the physical property or characteristic of the object may include detecting a change in electrical conductivity or resistance across the CNT network. In exemplary embodiments, a structural change to the CNT network, for example, on account of damage to the object, a change in shape of the object, or the like, may be detected based on the change in electrical conductivity or resistance. In other embodiments, a piezoresistive response of the CNT-network, for example on account of damage to the object, a change in shape of the object, propagation of an acoustic wave across the object or the like, may be detected based on the change in electrical conductivity or resistance. In yet other embodiments, a phase change of a substance on a surface of the object may be detected based on changes in surface conductivity or resistance. In some embodiments, detecting the change in the physical property or characteristic of the object may include isolating a electronic signal by applying one or more filters in the frequency domain. In exemplary embodiments, the physical property or characteristic of the object may be related to propagation of an acoustic wave across the object. Thus, in some embodiments, the detection system may be configured to detect the propagation of an acoustic wave across the object. In exemplary embodiments the physical property or characteristic of the object is related to structural health of the object. Thus, in some embodiments the detection system may be configured to detect damage to the object and/or determine severity, location, size, shape and distribution for the damage. In other embodiments the detection system may be configured to detect and/or locate an impact to the object. In exemplary embodiments, the detection system may be configured to detect and/or locate an impact to the object based on detection of the propagation of an acoustic wave generated by the impact. In exemplary embodiments, the physical property or characteristic of the object may be related to shape of the object. Thus, for example, the detection system may provide feedback on the shape of a configurable object. In exemplary embodiments, the detection system may be operationally coupled relative to the CNT network via one or more electrode arrays, for example, defining a plurality of electrode pairs across the CNT network.

In exemplary embodiments a system is disclosed including an object having a portion formed from a structured CNT-engineered material and one or more electrode arrays defining a plurality of electrode pairs across the CNT network. In some embodiments, data from each electrode pair may correspond to a different region of the object. For example, the plurality of electrode pairs may define a detection grid across the CNT network. In exemplary embodiments, the system may include one or more multiplexing switches for combining measurements from a plurality of the electrode pairs. In some embodiments, the one or more electrode arrays may be formed as traces using a direct-write technique. In other embodiments, the one or more electrode arrays may be formed using externally applied contacts. In some embodiments, the one or more electrode arrays may be formed using a flexible circuit. In exemplary embodiments, the one or more electrode arrays may be formed using a plurality of traces or layers. for example, wherein the traces are woven or braided.

In exemplary embodiments, a system is disclosed including an object having a portion formed from a structured CNT-engineered material that includes a structured CNT network, wherein the CNT network forms an antenna, for example, wherein the antenna is configured to receive, transmit, absorb and/or dissipate a signal, for example an electromagnetic signal (such as a radio signal or radar signal) an acoustic signal (such as a sonar signal) or an electrical signal (such as lightning). In exemplary embodiments the CNT network may be selectively patterned for specific applications, for example, for receiving or transmitting a radio signal, receiving or absorbing a radar signal, receiving or absorbing a sonar signal, or dissipating lightning.

In exemplary embodiments a system is disclosed including an object having at least a portion formed from a structured CNT-engineered material that includes a structured CNT network, wherein the CNT network is configured to function as a conductor for conveying thermal or electrical energy to or from one or more components coupled to the object. In some embodiments, the CNT network may be configured to transfer power to or from the one or more components, for example, wherein one of the components is a power source such as a solar power source. In other embodiments, the CNT network may be configured to convey communications to or from one or more components. In exemplary embodiments, the object may convey thermal energy so as to function as a heat sink, thermal radiator panel, thermal shield or the like.

Additional features, functions and benefits of the disclosed systems will be apparent from the description which follows, particularly when read in conjunction with the appended figures.

BRIEF DESCRIPTION OF THE DRAWINGS

FIG. 9 depicts temperature as a function of time over the first thirty seconds of heating exemplary objects at least part of which is formed of a structured CNT-engineered material including a structured CNT network for different ice thickness coating on the objects (no ice, 1, 2, and 3 mm) and different starting temperatures (−5, −10 and −15° C.), according to the present disclosure.

FIG. 14 steady state temperature as a function of power to the CNT-network and power as a function of applied voltage for an exemplary object at least part of which are formed of a structured CNT-engineered material including a structured CNT network, according to the present disclosure.

FIG. 15 anti-icing using the exemplary object of FIG. 14, according to the present disclosure.

DESCRIPTION OF EXEMPLARY EMBODIMENT(S)

Structured CNT-engineered materials represent a relatively new class of materials, exemplary embodiments of which are described, inter alia, in U.S. Pat. No. 7,537,825, PCT Application No. PCT/US2007/011913 (WO/2008/054541), U.S. application Ser. No. 11/895,621 (US 2008/0075954) and U.S. application Ser. No. 12/227,516 (US 2009/0311166). See also, Garcia E. J., Wardle, B. L., Hart J. A. and Yamamoto N., "Fabrication and multifunctional properties of a hybrid laminate with aligned carbon nanotubes grown in situ," *Composite Science and Technology*, v. 68, pp. 2034-41, 2008. Each of the foregoing patent and non-patent references is hereby incorporated herein to the extent that it is not inconsistent with the present disclosure. Structured CNT-engineered materials are discussed in greater detail below.

In general, structured CNT-engineered materials may advantageously include structured CNT networks, for example, wherein CNTs are structured relative to one another and/or with respect to a substrate. Thus, structured CNT-engineered materials may be distinguished from conventional CNT composites, for example, where the in conventional CNT composites CNTs are dispersed or grown such that the orientations of CNTs are substantially random in nature. As used herein, structured CNT-engineered materials are not limited to any particular CNT network morphology or CNT group morphology. For example, in some embodiments, a plurality of CNTs may be substantially aligned relative to one another. In other embodiments, a plurality CNTs may be substantially aligned relative to a substrate, for example, aligned radially relative to a fiber in a fiber reinforced composite.

It will be appreciated by one of ordinary skill in that are that groups of CNTs may include same or different alignments. For example, in some embodiments, a first plurality of CNTs (such as may be associated with a first substrate) may be aligned in a first direction and a second plurality of CNTs (such as may be associated with a second substrate) may be aligned in a second direction (which may be the same direction or a different direction than the first direction). In other embodiments, a first plurality of CNTs may be substantially aligned relative to a first substrate (for example, substantially perpendicular to a surface of the first substrate) and a second plurality of CNTs may be substantially aligned relative to a second substrate (for example, substantially perpendicular to a surface of the second substrate). In either case, the first plurality of CNTs may advantageously interact with the second plurality of CNTs to provide a contiguous CNT network, for example, between the first and second substrates.

Figure 1:
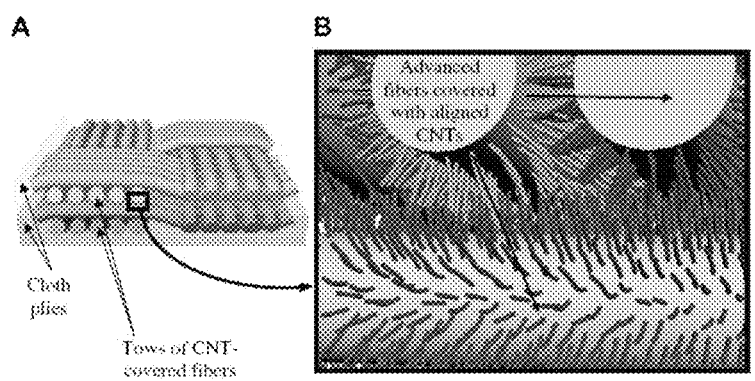
FIG. 1 depicts an exemplary morphology for fuzzy fiber reinforced composites, according to the present disclosure.
Figure 2:
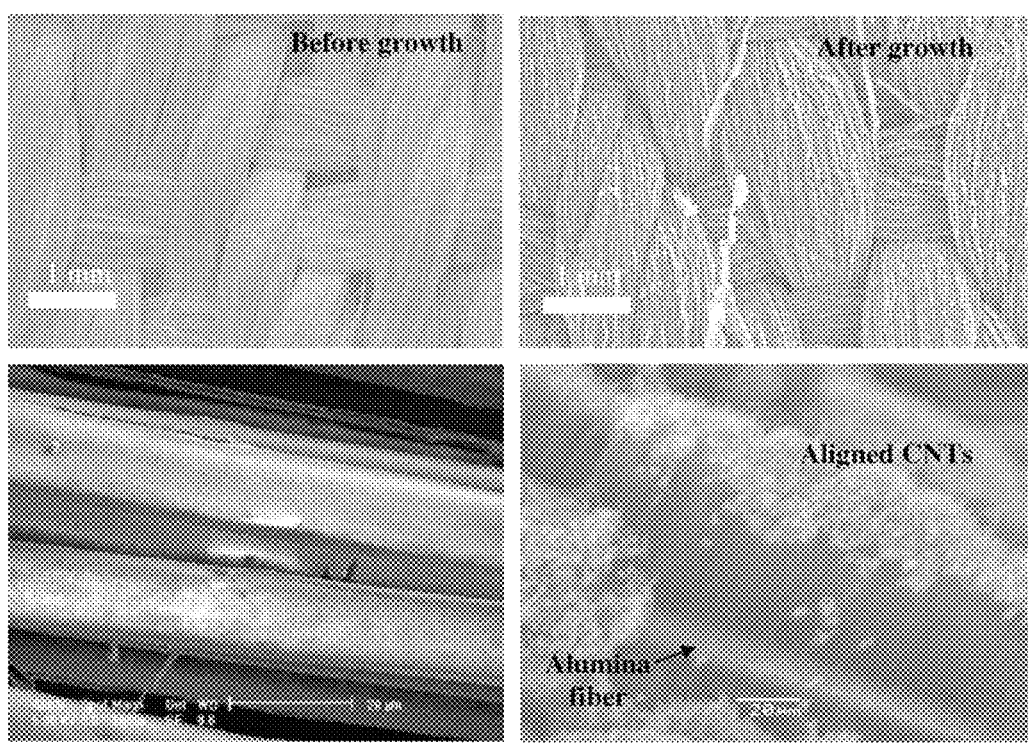
FIG. 2 depicts fibers for the fuzzy fiber reinforced composite of FIG. 1, before and after growth of a structured CNT network, according to the present disclosure.

In exemplary embodiments, structured CNT-engineered materials may be hybrid composites such as fiber reinforced hybrid composites. Fiber reinforced hybrid composites may include, for example, reinforcing fibers such as aluminum fibers (diameter typically of order microns) and structured CNTs (for example, with mass fraction between 0.5 and 2.5%) organized within a matrix (for example, a polymer matrix). As illustrated in FIGS. 1 and 2, CNTs may be structured with respect to the fibers (for example, grown in situ and radially aligned relative to the fibers) to form "fuzzy fibers" (FFs). Adjacent CNTs, for example, CNTs associated with adjacent FFs, may interact, for example, bind, to form the structured CNT network throughout the composite. Advantageously, the structured CNT network may be substantially uniform and contiguous. Composites formed using FFs may be referred to as fuzzy fiber reinforced composites (FFRCs).

Structured CNT-engineered materials may advantageously provide for improved electrical conductivity over conventional CNT and non-CNT composites. For example, whereas conventional composites typically exhibit electrical conductivity on the order of $10^{-7}$ to $10^{-10}$ S/mm, structured CNT-engineered materials may typically exhibit electrical conductivity on the order of $10^{-1}$ to $10^{-2}$ S/mm. Thus, in exemplary embodiments, structured CNT-engineered materials may exhibit conductivity greater than $10^{-5}$ S/mm and in some embodiments greater than $10^{-4}$ S/mm or less than $10^{-3}$ S/mm. FFRCs developed through Massachusetts Institute of Technologies Nano-Engineered Composite Aerospace Structures (NECST) consortium have been demonstrated to have substantially greater electrical conductivity (on the order of $10^8$ times greater for thru-thickness and $10^6$ times greater for in-plane) compared to similar composites without CNTs. Due to the structured CNT network, structured CNT-engineered materials may advantageously be substantially transversely isotropic with respect to electrical conductivity. In some embodiments, depending on morphology, structured CNT-engineered materials may be substantially isotropic with respect to electrical conductivity. The improved electrical conductivity of structured CNT-engineered materials is also particularly advantageous, for reducing a signal-to-noise ratio and achieving accurate/reliable detection and/or measurement of relatively small changes in resistance.

New and advantageous applications for structured CNT-engineered materials are disclosed herein. In some embodiments, systems are disclosed, wherein a structured CNT-engineered material may be used to construct an object capable of providing its own structural feedback, for example, structural health feedback. Advantageously, feedback may include spatial information, for example, for localizing a damaged area of the object. In other exemplary embodiments, systems are disclosed, wherein a structured CNT-engineered material may be used to construct an object capable of generating heat. The generated heat may be used, for example, for thermographic imaging of the object or other purposes, such as de-icing or maintaining a certain temperature. In yet other exemplary embodiments, systems are disclosed wherein a structured CNT-engineered material may be used to construct an object capable of functioning as an antenna, for example, for receiving, transmitting, absorbing and/or dissipating a signal. In still other embodiments, systems are discloses wherein, a structured CNT-engineered material may be used to construct an object capable of serving as a conduit for thermal or electrical energy.

Figure 3:
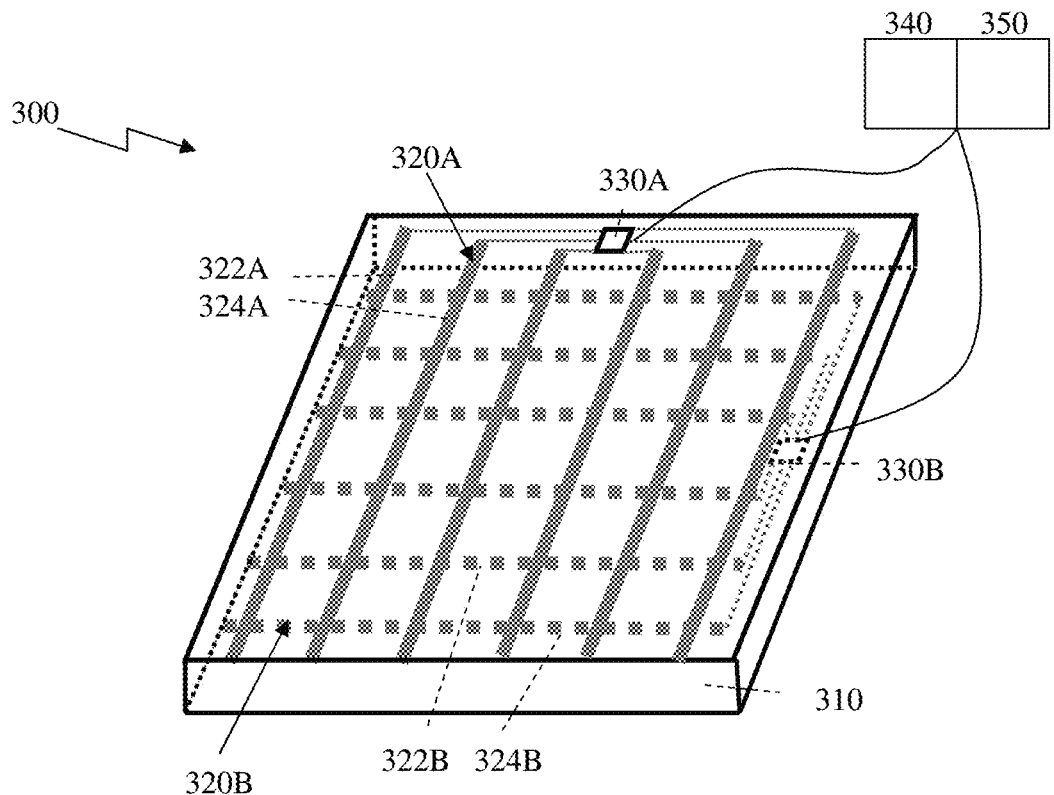
FIG. 3 depicts an exemplary system including an object at least portion of which is formed from a structured CNT-engineered material characterized by a structured CNT network, according to the present disclosure.

Referring now to FIG. 3, an exemplary system 300, according to the present disclosure, is depicted. The exemplary system 300 generally includes an object 310 at least portion of which is formed from a structured CNT-engineered material characterized by a structured CNT network. It is noted that object 310 may be any object and may stand-alone or be a component (structural or non-structural) of a larger assembly. By way of example, object 310 may be a wing of an aircraft, a siding of a building or a casing for a medical device.

In general, system 300 may include one or more electrodes operationally coupled relative to the structured CNT network, for example for detecting an electrical signal across the network. In exemplary embodiments system 300 may include one or more one or more electrode arrays defining a plurality of electrode pairs across the structured CNT network. The electrode pairs may advantageously define a grid across the structured CNT network. In exemplary embodiments, point wise stepping may be used to select and cycle through each of the electrode pairs. In other embodiments, a multiplexing switch may be used to combine measurements from a plurality of electrode pairs.

As depicted in FIG. 3, the system 300 includes pair of electrode arrays 320A and 320B positioned on opposite sides of the structured CNT network wherein one of the electrode arrays 320A includes a plurality of "active" electrode columns (for example, columns 322A and 324A) and the other electrode array 320B includes a plurality of "passive" (i.e., grounded) electrode rows (for example rows 322B and 324B). The columns and rows are each coupled by a multiplexing switch 330A or 330B. The electrode columns and rows advantageously define a detection grid, wherein each column/row electrode pair defines a point on the grid. By selecting and cycling through column/row electrode pairs, measurements, including spatial data, may be obtained for each of the grid points. It is also noted that in plane data may also be obtained, for example by selecting a pair of column electrodes or a pair of row electrodes for measurement. In some embodiments, a plurality of "active" electrodes may be aligned in rows and a plurality of "passive" (i.e., grounded) electrodes may be aligned in columns.

In exemplary embodiments, the electrode arrays 320A and 320B may be used to couple the structured CNT network to a detection system 340 and/or a control system 350 which may be implemented in whole or in part using a computing environment, or processor as described herein. In some embodiments the detection system 340 may be used to detect electrical conductivity/resistivity across one or more electrode pairs. In other embodiments the detection system 340 may be used to detect an electrical signal across the one or more electrode pairs. In some embodiments, the control system 350 may be used to power, for example, induce a voltage or current across, one or more electrode pairs, for example to generate heat.

In exemplary embodiments, the detection system 340 may be configured and/or programmed to detect a change in a physical property or characteristic of the object 310. In some embodiments the change in the physical property or characteristic of the object 310 may be determined by detecting a change in electrical conductivity/resistivity across the structured CNT network, (for example across, one or more electrode pairs). The changes in conductivity/resistivity may be on account of changes in the structured CNT network structure (for example, due to damage to object 310) or on account of a piezoresistive response of the structured CNT network structure (for example, due to propagation of a mechanical wave, a change of shape of the object 310, or structural damage to the object 310). In some embodiments, the detection system is configured and/or programmed to detect a phase change of a substance (for example, ice) on a surface of the object based on changes in surface conductivity or resistance.

In exemplary embodiments the physical property or characteristic of the object 310 may be related to the structural health of the object 310. Thus, for example, damage to the object 310 may be detected based on a detected change in conductivity/resistivity. Using a plurality of electrode pairs, for example, the electrode grid described above, spatial data for the damage may also be determined, for example relating to one or more of location, size, shape and distribution of the damage.

In other exemplary embodiments, the physical property or characteristic of the object may be related to the shape of the object 310. Thus, for example, a change to the shape of the object 310 may be detected based on a detected change in conductivity/resistivity. More particularly, a change in shape of the object 310 can cause a piezoresistive response which results in the change in conductivity/resistivity. This may be particularly useful for applications where the shape of the object 310 is configurable. In particular, the detection system 340 may provide useful feedback, to facilitate configuring the shape of the object 310.

In exemplary embodiments, changes in electrical conductivity/resistivity of the structured CNT network may also be used to detect and monitor, for example, based on a piezoresistive response, the propagation of a mechanical wave, for example an acoustic wave, through/across the object 310. Thus, the detection system 340 may be configured to detect an impact to the object 310 based on detection of a mechanical wave produced by the impact. Using a plurality of electrode pairs, spatial data for the impact may also be determined, for example relating to one or more of location, size, shape and distribution of the impact. In other embodiments, a mechanical wave may be generated and monitored in order to detect damage to the object 310, based on the propagation pattern of the wave. In exemplary embodiments the detection system 340 may include a plurality of acoustic sensors, coupled, at various points, to the structured CNT network. The plurality of acoustic sensors may be used to detect a propagating acoustic signal and determine its origin based on sensor timing. In exemplary embodiments, an acoustic wave may also be monitored using the structured CNT network as an acoustic-electric transducer. The electrical signal equivalent of the wave signal may advantageously be isolated in the frequency domain. An array of detectors may be used to track the spatial propagation of the signal. Acoustic wave applications are addressed in greater detail in sections which follow.

Figure 4:
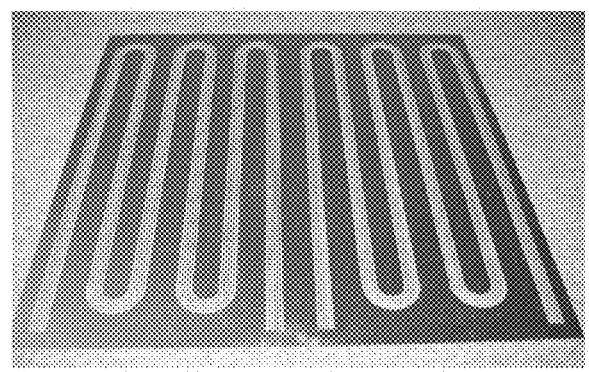
FIG. 4 depicts exemplary direct write traces produced using a plasma flame spray, according to the present disclosure.
Figure 5:
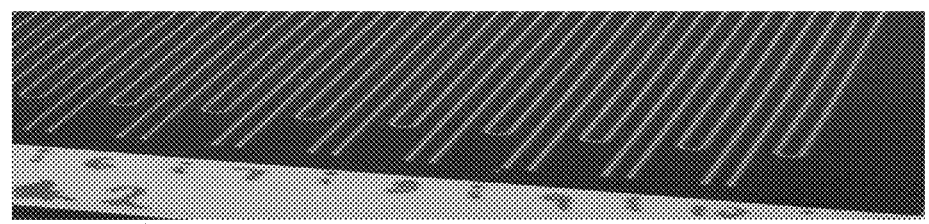
FIG. 5 depicts exemplary direct write traces produced using jetted atomized deposition, according to the present disclosure.

In exemplary embodiments, the electrode arrays 320A and 320B may be advantageously formed using a direct-write (DW) technique with a conductive material, for example, silver, onto a surface of the object 310. FIGS. 4 and 5 illustrate example of DW traces. More particularly, FIG. 4 depicts exemplary DW traces produced using a plasma flame spray (see U.S. Pat. No. 5,278,442) where copper or ceramic materials are electrically liquefied to be placed on the structure. FIG. 5 depicts exemplary DW traces produced using jetted atomized deposition (See U.S. Pat. No. 7,270,844) where silver or UV-curable epoxy are placed on a structure like an ink-jet printer and subsequently hardened. These references are incorporated herein to the extent they are not inconsistent with the present disclosure. DW technology advantageously enables a high level of electromechanical integration and facilitates coupling electrodes to a structured CNT network, particularly, where interconnection problems would otherwise exist (for example, in the absence of a free edge).

Figure 6:
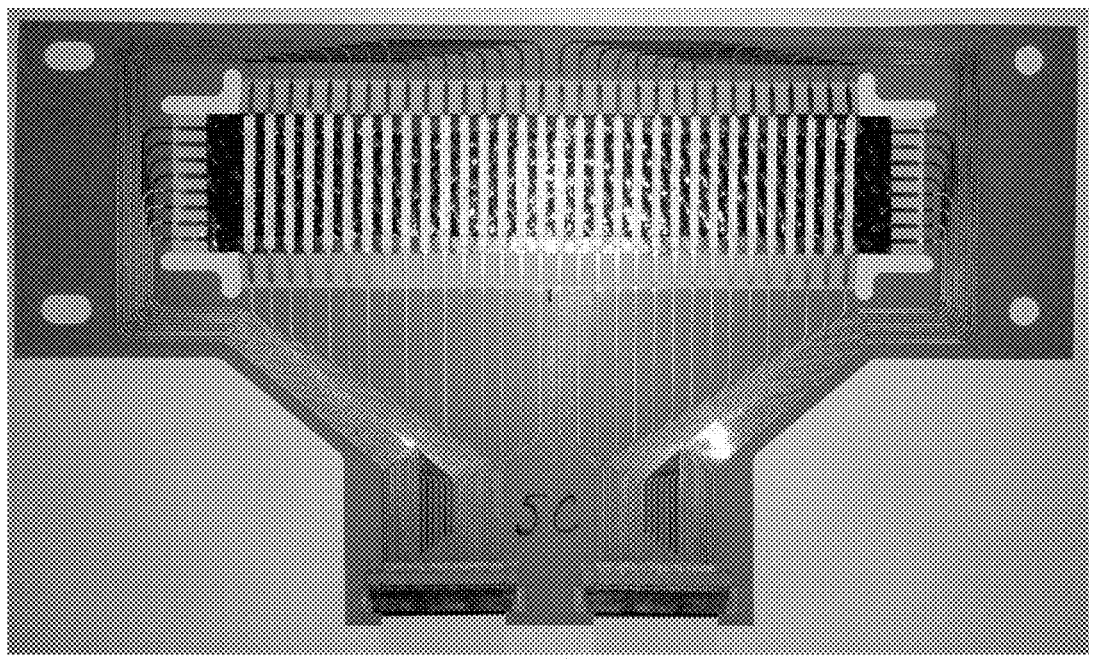
FIG. 6 depicts an exemplary flexible frame, according to the present disclosure.

Modifications to DW techniques are also possible. For example, a silk-screening process may be improved to reduce trace resistance variability and improve measurement accuracy. In some embodiments, a chemical etched template may be used to apply a trace pattern with better precision. In other embodiments, the number of traces (or electrodes) may be increased in order to increase spacial resolution (for example 32 horizontal (electrode rows) and 8 vertical (electrode columns). In exemplary embodiments, double-sided copper-coated-KAPTON (with coverlay) flexible circuit may be used to make connections with the DW traces (as apposed to soldered wire connections). The flexible circuit may be bonded first to the object and then the DW traces applied, including overwriting of the flexible circuit (which may, advantageously, include alignment marks). In exemplary embodiments, a urethane coating may be applied to prevent oxidation. In some embodiments, the flexible circuit may be configured in the shape of a rectangular frame, for example, with flaps on all 4 inside edges including exposed pads for the DW process. The object can fit inside the frame window with the top and bottom flap overlapping onto the front of the FFRP, and the left and right flap overlapping on the back of the FFRP. Traces can then be routed along the edges of the frame to an 80 pin ZIF connector located on a bottom tab for hardware connection. FIG. 6 depicts an exemplary flexible frame, according to the present disclosure. The exemplary flexible frame may provide enhanced electrical continuity (greater reliability, durability and consistency) between traces and a detection or control system, specifically because it can mitigate contract resistance issues.

As described herein a printed circuit board (PCB) may be configured to couple, e.g., with the flexible frame of FIG. 6. The PCB may advantageously include multiplexing switches, e.g., for multiplexing a plurality of channels (trace electrode pairs). The PCB may further be configured to couple with data acquisition hardware, a processor or computing environment. In exemplary embodiments, data may also be collected by hand, for example using a multimeter that can connect to the PCB as well. The data may then be transferred, for example to a processor or other computing environment for further processing. In other embodiments hardware, firmware and/or software may be implemented to automate the testing process (for example, automate selection and cycling of channels and/or data acquisition). In exemplary embodiments, automating hardware may connect directly to the flexible frame, for example, via a mating surface mount technology (SMT) header connector, and to a PC, for example, via a RS-232 connection. Dual multiplexer banks may be implemented to select an appropriate trace pair for measurement. A constant current may then be applied through the trace pair and voltage (for example, 16-bit voltage) measured. Conductivity/resistivity may then be derived (note that resistance is directly related to voltage over current). The forgoing technique allows fast measurement of traces. In tests conducted a total of 1140 measurements (including data from both ends of traces to eliminate constant offsets) were collected. Depending on settling time, test time may be as fast as 1 second for all measurements.

Validation tests for conductivity/resistivity measurement were performed using the embodiment depicted in FIG. 6. Each of three objects (specimens 1-3) were impacted at 15, 30 and 45 ft-lbs, with resistance data collected between each trial. Overall, the results from the refined setup served the intended purpose of validating this technique and demonstrating that the structured CNT network provides an excellent indication of barely visible impact damage (BVID). Furthermore, as can be seen in FIG. 7, the overwhelming outcome was that with each progressive impact level additional breakage of CNT links caused a nearly linear increase in peak percentage change of resistance value.

Figure 7:
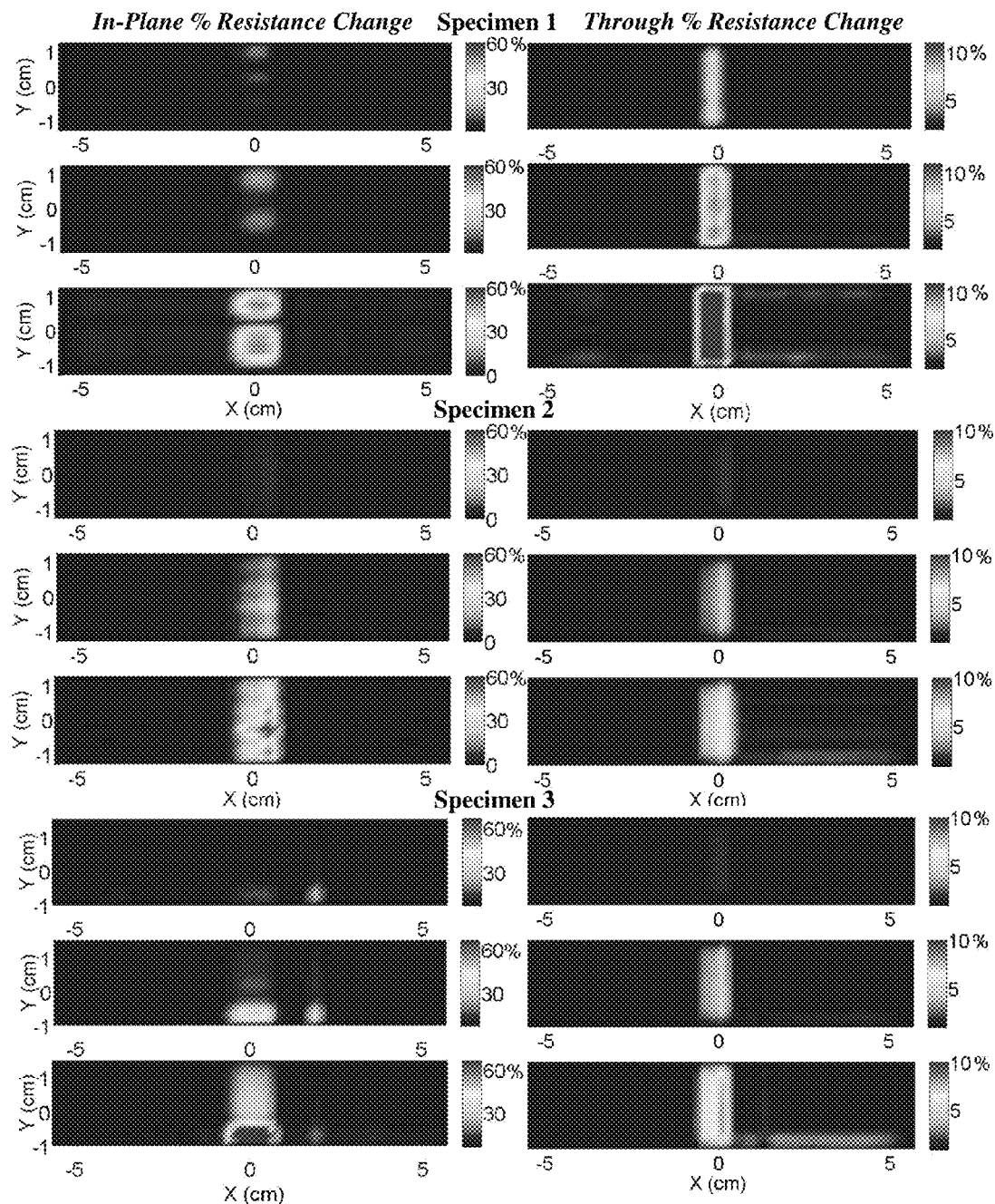
FIG. 7 depicts in-plane and though-plane conductivity reading for exemplary objects (specimens 1-3) formed from a structured CNT-engineered material and impacted at 15, 30 and 45 ft-lbs, respectively, according to the present disclosure.

As evidenced in FIG. 7, for in-plane resistance, the first (15 ft-lb) impact caused barely perceivable, but repeatable changes of ~10-20% in the impact region. The second (30 ft-lb) impact caused ~20-30% resistance change, and the final impact (45 ft-lb) ~40-60% change. In-plane results also appeared to be more localized to the actual impacted region, with clearly distinguishable damage patterns radiating from the impact center. Once locked into place, the impact location for progressive impacts on the same specimen was always in the same location, however, due to some play in the guiding system for the dropped weight the impact location specimen-to-specimen was not always in the same location. This effect can be seen most dramatically by comparing the second object (specimen 2), which had the best central alignment, with the third object (specimen 3), which was impacted towards the bottom edge. The specimen-to-specimen variability in measured damage was also likely influenced by the actual impact point, as a central impact would be more uniformly distributed in the specimen and cause less edge crushing.

For through-thickness results, the initial impact again caused small changes of ~2-4%, with the second impact causing ~4-8% changes and the final impact registering ~8-10% changes. In this case, the pattern of the results appeared to be much less sensitive to impact location, likely because these were narrow specimens, however, the damage severity measured did seem dependant on the impact point. No visible damage was present in any of these cases, however testing on witness specimens indicated that the specimens would completely fracture between 50-60 ft-lbs.

Acoustic Wave Detection:

In exemplary embodiments, a structured CNT network may be used to detect acoustic wave propagation in an object. In particular, a detection system including a plurality of microphones, accelerometers, or other acoustic sensors coupled at various points to the structured CNT network may be used to detect or "listen" for waves, e.g., high frequency stress waves (e.g., 30-300 kHz) reverberating in the structure, for example, radiating from an impact point. Using the time synchronized results from multiple sensors the generation point of the waves may be triangulated, for example in order to determine the impact point.

As noted above, acoustic wave detection may also be used as a possible solution for structured CNT network-based structural health monitoring, for example by exploiting the piezoresistive property of the CNTs. Essentially, as CNT fibers are strained by a stress wave, such as an acoustic wave, resistively dynamically proportionally to stress. Therefore, the response of a structured CNT-engineered material to an impact event can be captured through detection of a plurality of local CNT piezoresistive responses captured over a plurality of electrode pairs. It is noted that it may be advantageous to use a higher frequency acquisition system. The plurality of local CNT responses enables full-field visualization of the waves as they propagate from the point source. This may allow easy detection and locating of damage. In addition, since this technique uses high frequency data (e.g., >30 kHz), it can be much less susceptible to static, structural dynamic operating or acoustic loads, the effects of which can be filtered out in the frequency domain.

A preliminarily proof of concept experiment was conducted successfully to demonstrate the feasibility of this approach. Using a the small undamaged electroded FFRC specimen, a constant current source and an oscilloscope were connected to pairs of electrodes on either extreme of the specimen, in order to monitor the dynamic voltage response on the same time scale. Subsequently a pencil tip was broken in several places along the length of the specimen which would trigger the oscilloscope to capture data by the slight jump in voltage. By comparing the relative arrival times of the voltage peaks measured from either end of the specimen, the location of the pencil break could be easily determined.

Guided-Wave Detection

Relying on the piezoresistive property of the structured CNT network, Guided-Wave (GW) detection approaches may also be used. For example, a surface-bonded piezoelectric actuator may be used for high frequency GW excitation of an object. The response of the structured CNT network may then be captured (again advantageously using a higher frequency acquisition system). This approach may enable full-field visualization of a GW scatter field as it propagates.

Thermographic Techniques and De-Icing

As noted above, an object at least a portion of which is formed from or includes a structured CNT-engineered material including a structured CNT network may be coupled with a control system for providing power (voltage and/or current) to the structured CNT network so as to generate heat. Indeed, due to the nature of the CNTs having a reasonably low electrical resistance and high thermal conductivity, if a small voltage (such as 1-10 V) is applied across the structured CNT network (for example, across any electrode pair) the structured CNT-engineered material can isothermally raise its temperature relevantly quickly (for example, in seconds).

Figure 8:
FIG. 8 depicts thermographic imaging of an exemplary object at least part of which is formed of a structured CNT-engineered material including a structured CNT network, after heating the object using the structured CNT network, according to the present disclosure.

There are multiple advantages to the generating heart. Since structural non-uniformity can disrupt both the electrical and thermal flow in material, conventional thermographic imaging techniques may be applied, for example, to detect damage to the object. The structured CNT network fibers significantly enhances thermography by providing a fast internal heating source. For example, as seen in FIG. 8, a 2 V supply was placed across various electrode pairs on a previously impacted specimen and a thermal imaging camera was used to capture the response. As depicted, when the electrode pair away from the damage was utilized, no non-uniformities were observed beyond local heating near the electrodes. Subsequently, when the probes were placed at the extremes of the specimen, the impact damaged region became readily visible.

In other embodiments, generated heat may be used to heat the object or maintain the object at or above a selected temperature. In some embodiments, the object may be heated so as to heat a substance by proxy (for example, to induce a phase transition thereof) or maintain a substance at or above a selected temperature (for example to prevent a phase transition thereof). The substance may be external to a system, for example ice buildup, or internal to the system, for example fuel, coolant, etc). This may be particularly important to de-iceing, for example wherein the control system is configured and/or programmed to heat the object so as to de-ice the object, or wherein the control system is configured and/or programmed to maintain the object at or above a selected temperature to prevent icing. In exemplary embodiments, a detection system may be included for providing temperature feedback for either the object or its surroundings. The control system may be configured and/programmed to adjust the power (current and/or voltage) based on the temperature feedback. In exemplary embodiments, the temperature feedback may include a temperature rate of change, for example, a heating rate of change or cooling rate of change (such as after heating), for the object or for a substance heated by proxy thereof. In some embodiments, the detection system may be configured and/or programmed to determine, based on the temperature rate of change, a property or characteristic (for example, presence, amount, temperature, constitution/classification, or the like) of a substance heated by the object. For example, the detection system may be configured and/or programmed to determine a presence (or absence) of a substance, for example ice, on in or otherwise thermally coupled to the object based on, for example a temperature change rate for the object being less than a predetermined value. The detection may further be configured to determine an amount, for example a thickness, mass, volume, or the like, of the substance based on, for example the temperature change rate for the object. In some embodiments, changes in a temperature change rate may be indicative of changes in an amount of a substance. In other embodiments a temperature rate of change may be correlated, for example, directly or indirectly, to the amount of a substance. In some embodiments, a starting temperature may be considered in conjunction with a temperature rate of change when determining the amount of a substance. Further exemplary embodiments for using temperature rate of change and experimental results are presented below.

Thermodynamic modeling may be used to demonstrate a correlation between temperature rate of change and substance amount. Consider, for example, a body comprised of n discrete materials immersed in a fluid of temperature $T_0$. The body is heated by volumetric heating and cooled by convective heat transfer. Placing a control volume around the system, the energy flow is given by the first law of thermodynamics:

$$\dot{E}_{in}(t) + \dot{E}_{gen}(t) = \dot{E}_{sto}(t) + \dot{E}_{out}(t) \tag{1}$$

where t is time, $\dot{E}_{in}(t)$ is the rate of energy entering the control volume, $\dot{E}_{gen}(t)$ is the rate of energy generated within the control volume, $\dot{E}_{sto}(t)$ is the rate of energy stored within the control volume, and $\dot{E}_{out}(t)$ is rate of energy leaving the control volume. Let us assume that no energy is entering the control volume except through volumetric heating:

$$\dot{E}_{in}(t) = 0 \quad \dot{E}_{gen}(t) = \int_V Q(\vec{x}, t) dV \tag{2}$$

where Q is the volumetric heating rate and $\vec{x}$ is the position. If no phase transitions occur within the control volume, the rate of energy stored is:

$$\dot{E}_{sto}(t) = \int_V \rho \, c \, \frac{dT(\vec{x}, t)}{dt} dV \tag{3}$$

where $\rho$ is the mass density, and c is the specific heat per unit mass, and T is temperature. The rate of energy leaving the control volume is given by:

$$\dot{E}_{out}(t) = \int_A \vec{q}(\vec{x}, t) \cdot \vec{n}(\vec{x}) dA \tag{4}$$

where q is the heat flux vector, and n is the outward normal vector. If heat is lost only through convection, the normal heat flux is given by:

$$\vec{q}(\vec{x}, t) \cdot \vec{n}(\vec{x}) = h(\vec{x})[T(\vec{x}, t) - T_0] \tag{5}$$

where h is the convection coefficient. The system is initially at thermal equilibrium with ambient conditions. At time zero, a constant electrical power P is applied to the body to heat it. Thus the rate of energy generated within the control volume equals the input electrical power:

$$\dot{E}_{gen}(t) = P \tag{6}$$

Let us assume that the n discrete materials are infinitely conducting, and therefore the temperature of the body is independent of position.

$$T(\vec{x}, t) = T(t) = \tag{7}$$

Also, let us assume that that the convection coefficient, density, and specific heat are dependent only on the material number. With these assumptions, the rate of stored and output energy terms, Equations 3 and 4, are given by:

$$\dot{E}_{sto}(t) = \left[\sum_{i=1}^{n} \rho_i \, c_i \, V_i\right] \frac{dT(t)}{dt} \quad \dot{E}_{out}(t) = \left[\sum_{i=1}^{n} h_i \, A_i\right](T(t) - T_0) \tag{8}$$

Where i subscript indicates the parameter is for the $i^{th}$ material. Materials internal to the body have a convection coefficient of zero since integration in Equation 4 is performed over the control area. It should be noted that the mass of material i is given by:

$$m_i = V_i \rho_i \tag{9}$$

Solving Equation 1 for temperature, and using Equation 6-9:

$$T(t) = T_0 + P(1 - e^{-t\lambda}) / \sum_{i=1}^{n} h_i \, A_i \tag{10}$$

where the exponential decay constant $\lambda$ is given by:

$$\lambda = \sum_{i=1}^{n} h_i \, A_i / \sum_{i=1}^{n} m_i \, c_i \tag{11}$$

It should be noted that the derivative of the temperature at time equals zero is given by:

$$\left. \frac{dT}{dt} \right|_{t=0} = P / \sum_{i=1}^{n} m_i \, c_i \tag{12}$$

Note that Equation 12 is independent of the convection coefficient. Thus two samples with different convection boundary conditions will have the same initial slope, assuming the same power is applied. Consider two bodies starting at temperature $T_0$ and heated with power P. The first body has n materials, and the second body has one additional material. The ratio of the initial slope is given by:

$$\frac{\left.\frac{dT}{dt}\right|_{t=0} (n \text{ materials})}{\left.\frac{dT}{dt}\right|_{t=0} (n+1 \text{ materials})} = \frac{P}{\sum_{i=1}^{n} m_i \, c_i} \cdot \frac{\sum_{i=1}^{n+1} m_i \, c_i}{P} = 1 + \frac{m_{n+1} \, c_{n+1}}{\sum_{i=1}^{n} m_i \, c_i} \tag{13}$$

Since the specific heat and mass are greater than zero for all materials, the ratio in Equation 13 is greater than one. Thus the slope (temperature rate of change) decreases as an additional substance or material (such as ice or water) is added to the body. This correlation may be used to determine if and in what amount a substance or material has been added to a system.

Figure 10:
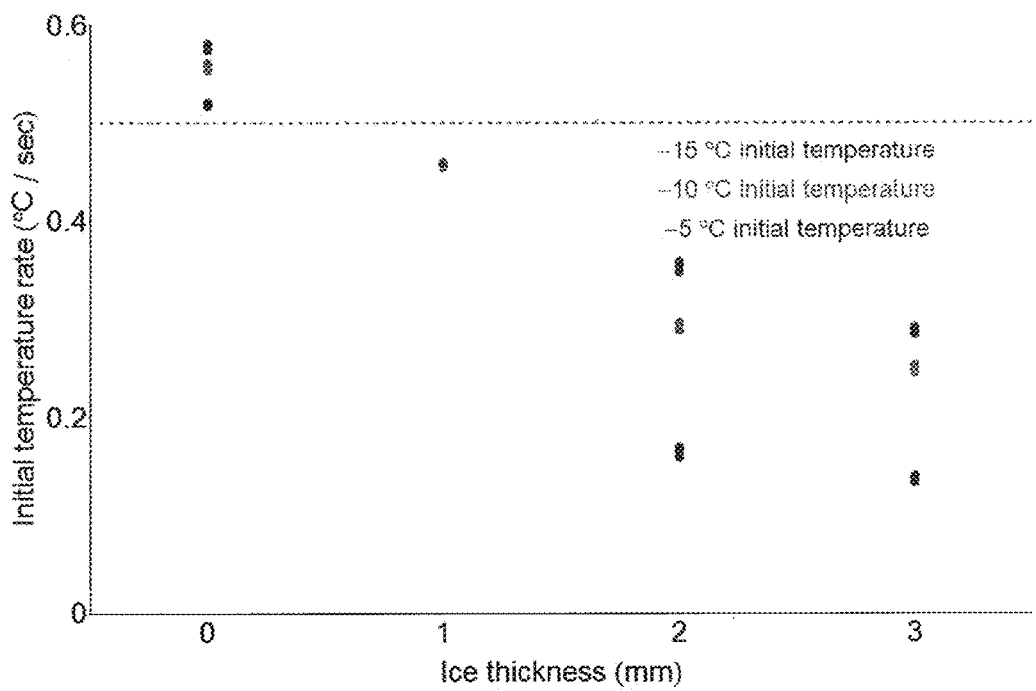
FIG. 10 depicts temperature rate of change as a function of ice thickness for the exemplary objects and data of FIG. 9, according to the present disclosure.

To illustrate detection of ice using the above principles, temperature as a function of time over the first thirty seconds for heating specimens of different ice thickness (no ice, 1, 2, and 3 mm) and starting temperature (−5, −10 and −15° C.), is plotted in FIG. 9. For the first approximately twenty seconds of data, the temperature change rate appears nearly linear. The first twenty points of the temperature data was fitted to a line. The slope of this line (i.e. the temperature rate of change) is plotted as a function of ice thickness in FIG. 10. As can be seen in FIG. 10, as the ice thickness increases the temperature rate of change decreases, regardless of starting temperature (this was predicted by Equation 13). For all samples with no ice, the temperature rate of change is above 0.5° C./sec, which is indicated by the dashed horizontal line. Temperature rate of change is also shown to be dependent on starting temperature which is not predicated in Equation 13. Possible reasons include that the specific heat or convection coefficient is temperature dependent, or that there is a thermal lag in the system which is not accounted for in the equations.

Figure 11:
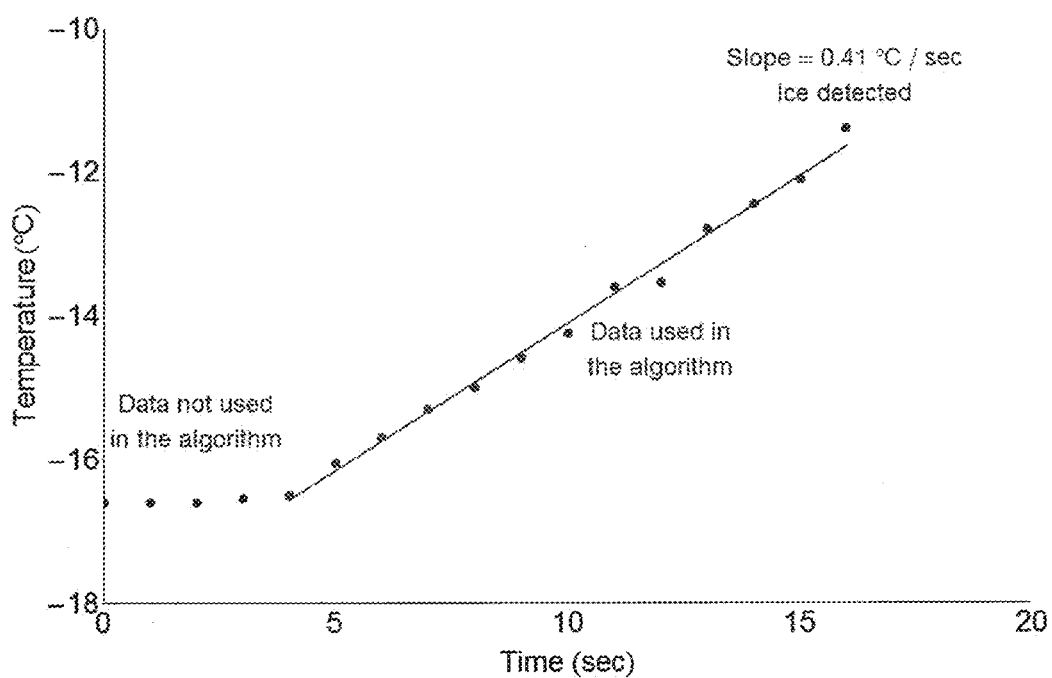
FIG. 11 depicts an exemplary implementation of an ice detection technique, wherein ice was detected, according to the present disclosure.
Figure 12:
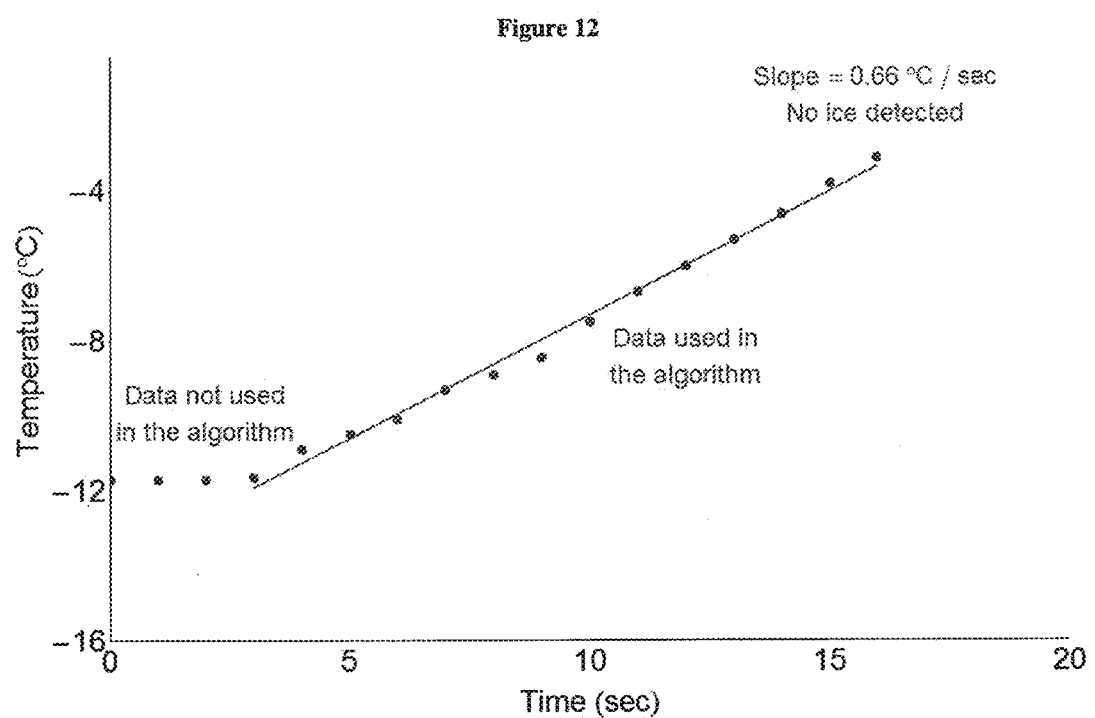
FIG. 12 depicts an exemplary implementation of an ice detection technique, wherein ice was not detected, according to the present disclosure.

Based one the above results, a simple ice detection technique may be implemented. A constant or near constant power (for example, 10 W) may be supplied to a structured CNT network of an object and temperature rate of change is calculated (for example, based on temperature as a function time over the first fifteen seconds). In some embodiments, it may be beneficial to discard data where temperature rate of change is less than 0.15° C. and use only the remaining data in calculating temperature rate of change. Ice is then detected if the temperature change rate is less than 0.5° C./sec. Exemplary implementation of the above ice detection technique is illustrated in FIGS. 11 and 12. FIG. 11 depicts an implementation where ice was detected. FIG. 12 depicts an implementation where no ice was detected.

De-icing tests were performed measuring temperature as a function of time during the de-icing of specimens of varying ice thicknesses (water depth) and starting temperature (see Table 1 for specific parameters):

TABLE 1

De-icing test matrix

| | | Start temperature | | |
|---|---|---|---|---|
| | | −5° C. | −10° C. | −15° C. |
| Water depth | 0 mm | 3 tests | 3 tests | 3 tests |
| | 1 mm | — | — | 3 tests |
| | 2 mm | 3 tests | 3 tests | 3 tests |
| | 3 mm | 3 tests | 3 tests | 3 tests |

Figure 13:
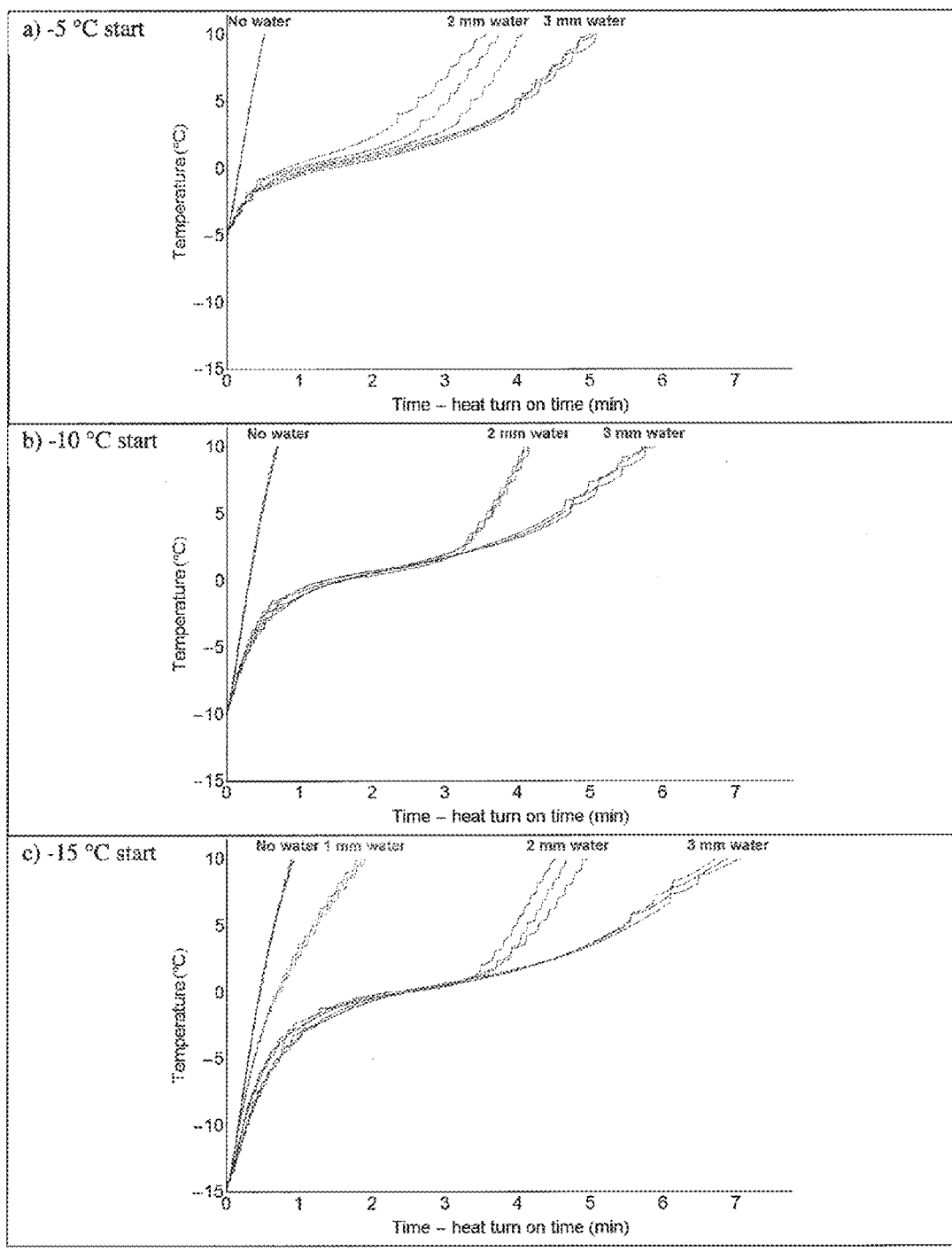
FIG. 13 depicts de-icing of exemplary objects at least part of which are formed of a structured CNT-engineered material including a structured CNT network, wherein the objects are heated using the structured CNT network, according to the present disclosure.
Figure 16:
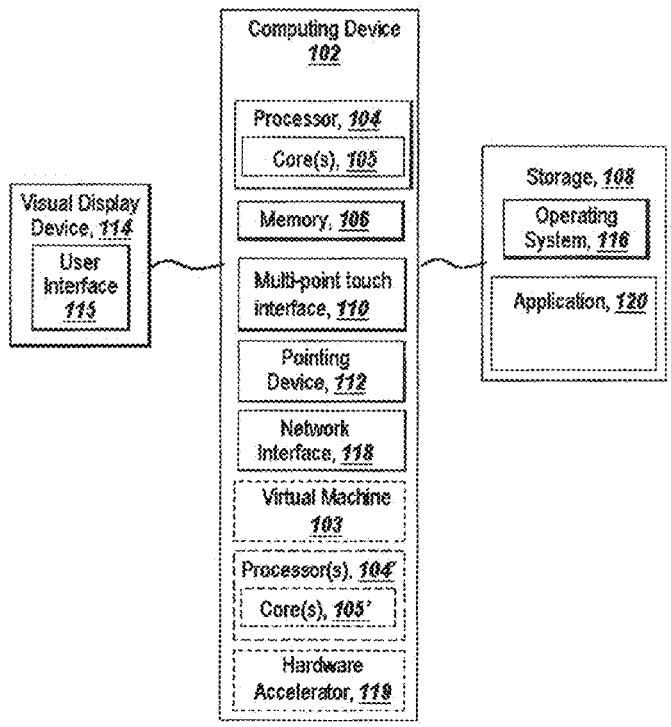
FIG. 16 depicts an exemplary computing environment according to the present disclosure.
Figure 17:
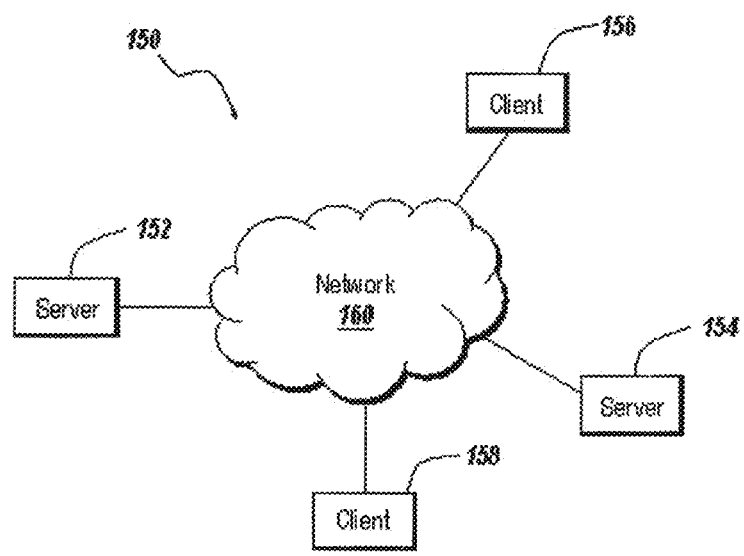
FIG. 17 depicts an exemplary network environment, according to the present disclosure.

The results of the deicing tests are depicted in FIG. 13. As can be seen in FIG. 13, as ice thickness increases the temperature change rate at a given temperature decreases. Also of interest in FIG. 13 is de-icing time which may be defined, for example, as the amount time it takes the object to reach the melting point of a substance (0° C. for ice) or, alternatively, the amount time it takes the object reach a selected temperature above the melting point (for example, 5° C.). As depicted in FIG. 13, de-icing time increased as a function of thickness and decreased as a function starting temperature.

In exemplary embodiments, power required to prevent a substance (for example water), on, in or otherwise thermally coupled to an object, from freezing or re-refreezing may be determined. In particular, various levels of power may be applied to a structured CNT network of an object to determine or maintain corresponding steady state temperatures for that object (note that steady state temperature is not affected by the presence or absence of ice). FIG. 14, depicts steady state temperature as a function of power and power as a function of applied voltage for an exemplary object. Data was collected over a 30 minute period for each power level. As can be seen in FIG. 14, both the temperature versus power and power versus applied voltage appear nearly linear.

As depicted in FIG. 14, the steady state temperature of 0° C. corresponded to approximately 1.81 W of power for the exemplary object. Anti-icing was tested using 2 W of power (steady state value of approximately 3° C.). Two types of tests were performed to investigate anti-icing performance; the first was anti-icing starting at 5° C. following cool down from room temperature, and the second was anti-icing starting at 5° C. following warm-up (de-icing) from −5° C.). The results of the tests are depicted in FIG. 15. In each case the predicted steady state temperature was achieved.

Additional Applications.

In exemplary embodiments, an object at least a portion of which is formed from or includes a structured CNT-engineered material having a structured CNT network may be used/configured as an antenna, for example, for receiving, transmitting, absorbing or dissipating electromagnetic radiation, acoustic radiation or electrical discharge. Advantageously, the structured CNT network may be selectively structured so as to optimize the structure, conductivity or other characteristic or property of the antenna for a given application or purpose. In exemplary embodiments, the electromagnetic radiation may be a radio signal or radar signal, for example, wherein the structured CNT network is selectively patterned for radio detection/transmission and/or radar detection/dispersion. In other exemplary embodiments, the acoustic radiation may from sound propagation, such as sonar, for example, wherein the structured CNT network is selectively patterned for sonar detection. In yet other exemplary embodiments the electrical discharge or energy transfer may be a high power discharge, such as lightning, for example, wherein the structured CNT network is selectively patterned for lightning dissipation.

In some embodiments an object at least a portion of which is formed from or includes a structured CNT-engineered material having or includes a structured CNT network may be used/configured as a conduit for conveying thermal or electrical energy, for example between a plurality of components coupled to the object. In exemplary embodiments, the coupled CNT network may be configured to provide power transfer from one component (for example, from a solar power source) to another component. In other exemplary embodiments, the coupled CNT network may be configured provide a communication pathway between components. In exemplary embodiments, based on the high thermal conductivity of the structured CNT network, the object may be used as a heat sink or radiator panel. In other embodiments the object may be used as a heat shield or other thermal protecting device.

Machine Embodiments

It is contemplated that detection and control systems presented may be implemented, in part, e.g., via one or more programmable processing units having associated therewith executable instructions held on one or more non-transitory computer readable medium, RAM, ROM, harddrive, and/or hardware. In exemplary embodiments, the hardware, firmware and/or executable code may be provided, e.g., as upgrade module(s) for use in conjunction with existing infrastructure (e.g., existing devices/processing units). Hardware may, e.g., include components and/or logic circuitry for executing the embodiments taught herein as a computing process.

Displays and/or other feedback means may also be included to convey detected/processed data. Thus, in exemplary embodiments, structural health information, shape information, acoustic wave propagation, thermal information, etc. may be displayed, e.g., on a monitor. The display and/or other feedback means may be stand-alone or may be included as one or more components/modules of the processing unit(s). In exemplary embodiments, the display and/or other feedback means may be used to visualize structural damage to an object.

The software code or control hardware which may be used to implement some of the present embodiments is not intended to limit the scope of such embodiments. For example, certain aspects of the embodiments described herein may be implemented in code using any suitable programming language type such as, for example, C or C++ using, for example, conventional or object-oriented programming techniques. Such code is stored or held on any type of suitable non-transitory computer-readable medium or media such as, for example, a magnetic or optical storage medium.

As used herein, a "processor," "processing unit," "computer" or "computer system" may be, for example, a wireless or wireline variety of a microcomputer, minicomputer, server, mainframe, laptop, personal data assistant (PDA), wireless e-mail device (e.g., "BlackBerry" trade-designated devices), cellular phone, pager, processor, fax machine, scanner, or any other programmable device configured to transmit and receive data over a network. Computer systems disclosed herein may include memory for storing certain software applications used in obtaining, processing and communicating data. It can be appreciated that such memory may be internal or external to the disclosed embodiments. The memory may also include non-transitory storage medium for storing software, including a hard disk, an optical disk, floppy disk, ROM (read only memory), RAM (random access memory), PROM (programmable ROM), EEPROM (electrically erasable PROM), etc.

Referring now to FIG. 9, an exemplary computing environment suitable for practicing exemplary embodiments is depicted. The environment may include a computing device 102 which includes one or more non-transitory media for storing one or more computer-executable instructions or code for implementing exemplary embodiments. For example, memory 106 included in the computing device 102 may store computer-executable instructions or software, e.g. instructions for implementing and processing an application 120. For example, execution of application 120 by processor 104 may facilitate detection of electrical conductivity across a structured CNT network.

The computing device 102 also includes processor 104, and, one or more processor(s) 104' for executing software stored in the memory 106, and other programs for controlling system hardware. Processor 104 and processor(s) 104' each can be a single core processor or multiple core (105 and 105') processor. Virtualization can be employed in computing device 102 so that infrastructure and resources in the computing device can be shared dynamically. Virtualized processors may also be used with application 120 and other software in storage 108. A virtual machine 103 can be provided to handle a process running on multiple processors so that the process appears to be using only one computing resource rather than multiple. Multiple virtual machines can also be used with one processor. Other computing resources, such as field-programmable gate arrays (FPGA), application specific integrated circuit (ASIC), digital signal processor (DSP), Graphics Processing Unit (GPU), and general-purpose processor (GPP), may also be used for executing code and/or software. A hardware accelerator 119, such as implemented in an ASIC, FPGA, or the like, can additionally be used to speed up the general processing rate of the computing device 102.

The memory 106 may comprise a computer system memory or random access memory, such as DRAM, SRAM, EDO RAM, etc. The memory 106 may comprise other types of memory as well, or combinations thereof. A user may interact with the computing device 102 through a visual display device 114, such as a computer monitor, which may display one or more user interfaces 115. The visual display device 114 may also display other aspects or elements of exemplary embodiments (for example, thermographic images of an object. The computing device 102 may include other I/O devices such a keyboard or a multi-point touch interface 110 and a pointing device 112, for example a mouse, for receiving input from a user. The keyboard 110 and the pointing device 112 may be connected to the visual display device 114. The computing device 102 may include other suitable conventional I/O peripherals. The computing device 102 may further comprise a storage device 108, such as a hard-drive, CD-ROM, or other storage medium for storing an operating system 116 and other programs, e.g., application 120 characterized by computer executable instructions for implementing the detection and control systems described herein.

The computing device 102 may include a network interface 118 to interface to a Local Area Network (LAN), Wide Area Network (WAN) or the Internet through a variety of connections including, but not limited to, standard telephone lines, LAN or WAN links (e.g., 802.11, T1, T3, 56 kb, X.25), broadband connections (e.g., ISDN, Frame Relay, ATM), wireless connections, controller area network (CAN), or some combination of any or all of the above. The network interface 118 may comprise a built-in network adapter, network interface card, PCMCIA network card, card bus network adapter, wireless network adapter, USB network adapter, modem or any other device suitable for interfacing the computing device 102 to any type of network capable of communication and performing the operations described herein. Moreover, the computing device 102 may be any computer system such as a workstation, desktop computer, server, laptop, handheld computer or other form of computing or telecommunications device that is capable of communication and that has sufficient processor power and memory capacity to perform the operations described herein.

The computing device 102 can be running any operating system such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, any operating systems for mobile computing devices, or any other operating system capable of running on the computing device and performing the operations described herein. The operating system may be running in native mode or emulated mode.

FIG. 10 illustrates an exemplary network environment 150 suitable for a distributed implementation of exemplary embodiments. The network environment 150 may include one or more servers 152 and 154 coupled to clients 156 and 158 via a communication network 160. In one implementation, the servers 152 and 154 and/or the clients 156 and/or 158 may be implemented via the computing device 102. The network interface 118 of the computing device 102 enables the servers 152 and 154 to communicate with the clients 156 and 158 through the communication network 160. The communication network 160 may include Internet, intranet, LAN (Local Area Network), WAN (Wide Area Network), MAN (Metropolitan Area Network), wireless network (e.g., using IEEE 802.11 or Bluetooth), etc. In addition the network may use middleware, such as CORBA (Common Object Request Broker Architecture) or DCOM (Distributed Component Object Model) to allow a computing device on the network 160 to communicate directly with another computing device that is connected to the network 160.

In the network environment 160, the servers 152 and 154 may provide the clients 156 and 158 with software components or products under a particular condition, such as a license agreement. The software components or products may include one or more components of the application 120. For example, the client 156 may detect electrical conductivity data which is subsequently communicated over the server 152 for processing.

Although the teachings herein have been described with reference to exemplary embodiments and implementations thereof, the disclosed systems are not limited to such exemplary embodiments/implementations. Rather, as will be readily apparent to persons skilled in the art from the description taught herein, the disclosed systems are susceptible to modifications, alterations and enhancements without departing from the spirit or scope hereof. Accordingly, all such modifications, alterations and enhancements within the scope hereof are encompassed herein.

What is claimed is:

1. An apparatus comprising:
an object having a portion formed from a carbon nanotube (CNT) engineered material having a CNT network formed of a first plurality of CNTs bound to one another by attraction or entanglement to form a self-supporting sheet free of a support material prior to contact with a matrix material, the CNT network conducts electricity to maintain or change a temperature of the portion of the object in a predetermined temperature pattern, wherein the first plurality of CNTs are distributed to form a contiguous network of CNTs;
a first electrical contact coupled to a first portion of the CNT network;
a second electrical contact coupled to a second portion of the CNT network; and
wherein the first electrical contact and the second electrical contact are couplable to a control system configured or programmed to drive the CNT network with electrical energy to generate heat across the CNT network in the pre-determined temperature pattern.

2. The apparatus of claim 1, wherein the CNT network has a structured form to define a geometry for the material and allow physical manipulation thereof.

3. The apparatus of claim 1, wherein the control system drives the CNT network with the electrical energy to increase or maintain a temperature of a substance associated with the object at or above a selected temperature.

4. The apparatus of claim 1, wherein the control system drives the CNT network with the electrical energy to increase the temperature of the portion of the object so as to de-ice the portion of the object or prevent icing on the portion of the object.

5. The apparatus of claim 1, wherein the control system drives the CNT network with the electrical energy to increase the temperature of the portion of the object to prevent icing thereof.

6. The apparatus of claim 1, wherein the control system drives the CNT network with the electrical energy to increase the temperature of the portion of the object to melt a frozen fluid or prevent a fluid from freezing.

7. The apparatus of claim 1, further comprising a detection system for providing temperature feedback for at least one of the object or its surroundings.

8. The apparatus of claim 7, wherein the electrical energy from the control system is adjustable based on the temperature feedback.

9. The apparatus of claim 7, wherein the temperature feedback indicates a temperature rate of change for an interior or exterior portion of the object or for a substance heated by the object.

10. The apparatus of claim 9, wherein the detection system determines an amount of ice on the exterior portion of the object based on the temperature rate of change.

11. The apparatus of claim 7, wherein the detection system detects a phase change of a substance on a surface of the object based on changes in electrical conductivity or resistance across the CNT network.

12. The apparatus of claim 1, wherein the first plurality of CNTs in the CNT network interact with a second plurality of CNTs in the CNT network to provide a contiguity between the first and second pluralities of CNTs.

13. The apparatus of claim 1, wherein an electrical conductivity of the apparatus is between $10^{-4}$ S/mm and $10^{-1}$ S/mm.

14. A system comprising:
an object having a portion formed from a carbon nanotube (CNT) engineered material having a CNT network formed of a first plurality of CNTs bound to one another by attraction or entanglement to form a self-supporting sheet free of a support material prior to contact with a matrix material, the CNT network conducts electricity, wherein the first plurality of CNTs are distributed to form a contiguous network of CNTs;
a first electrical contact coupled to a first portion of the CNT network;
a second electrical contact coupled to a second portion of the CNT network; and
a configurable or programmable detection system couplable to the first electrical contact and the second electrical contact to detect a change in a physical property or characteristic related to a change in structure of the object, based on a measurement across a portion of the CNT network;
wherein detecting the change in the physical property or the characteristic includes detecting at least one of: (i) a change in electrical conductivity or resistance across the portion of the CNT network or (ii) a propagation of an acoustic wave across a portion of the object.

15. The system of claim 14, wherein the CNT network has a structured form to define a geometry for the material and allow physical manipulation thereof.

16. The system of claim 14,
wherein the physical property or characteristic is related to structural health of the object, and
wherein the structural change to the CNT network is on account of damage to the object.

17. The system of claim 14,
wherein the physical property or characteristic is related to a shape of the object, and
wherein the structural change to the CNT network is on account of a change in the shape of the object.

18. The system of claim 17,
wherein the shape of the object is configurable, and wherein the detection system provides feedback on the shape of the object.

19. The system of claim 14, wherein the detection system is couplable to the CNT network via one or more electrode arrays defining a plurality of electrode pairs across the CNT network.

20. The system of claim 19, further comprising one or more multiplexers for combining measurements from the plurality of the electrode pairs.

21. The system of claim 14, wherein the detection system detects a phase change of a substance on a surface of the object based on changes in electrical conductivity or resistance across the CNT network.

22. A method for controlling the temperature of an object, the method comprising:
    providing an object having a portion formed from a carbon nanotube (CNT) engineered material having a CNT network formed of a plurality of CNTs bound to one another by attraction or entanglement to form a self-supporting sheet free of a support material prior to contact with a matrix material, the CNT network conducts electricity, wherein the plurality of CNTs are distributed to form a contiguous network of CNTs, wherein the object includes:
        a first electrical contact coupled to a first portion of the CNT network; and
        a second electrical contact coupled to a second portion of the CNT network;
    providing a control system operationally couplable to the first electrical contact and the second electrical contact; and
    instructing the control system to drive the CNT network with electrical energy to generate heat across the CNT network so as to maintain or change a temperature of the object in a pre-determined temperature pattern.

23. The method of claim 22, wherein the CNT network has a structured form to define a geometry for the material and allow physical manipulation thereof.

24. The method of claim 22, further comprising instructing the control system to drive the CNT network with electrical energy to generate heat to increase or maintain a temperature of a substance associated with the object at or above a selected temperature.

25. The method of claim 24, wherein increasing or maintaining a temperature of the substance is configured to affect a phase change in the substance.

26. The method of claim 22, further comprising instructing the control system to drive the CNT network with electrical energy to increase the temperature of the object so as to de-ice a portion of the object or prevent icing on a portion of the object.

27. The method of claim 22, further comprising instructing the control system to drive the CNT network with electrical energy to increase the temperature of a portion of the object to melt a frozen fluid in the system or prevent a fluid in the system from freezing.

28. The method of claim 22, further comprising detecting temperature feedback for at least one of the object and its surroundings, wherein the control system adjusts the electrical energy based on the temperature feedback.

29. The method of claim 22, further comprising determining a property or characteristic of a substance heated by the object based on a temperature rate of change for at least a portion of the object or for the substance heated by the object.

30. A method for de-icing or preventing icing of an object, the method comprising:
    providing an object having a portion formed from a carbon nanotube (CNT) engineered material having a CNT network formed of a first plurality of CNTs bound to one another by attraction or entanglement to form a self-supporting sheet free of a support material prior to contact with a matrix material, the CNT network conducts electricity to maintain or change a temperature of the portion of the object in a predetermined temperature pattern, wherein the first plurality of CNTs are distributed to form a contiguous network of CNTs, wherein the object includes:
        a first electrical contact coupled to a first portion of the CNT network; and
        a second electrical contact coupled to a second portion of the CNT network;
    providing a control system operationally couplable to the first electrical contact and the second electrical contact; and
    instructing the control system to drive the CNT network with electrical energy to generate heat across the CNT network so as to increase the temperature of the object in the pre-determined temperature pattern, so as to de-ice at least the portion of the object or prevent icing on the portion of the object.

* * * * *